(12) United States Patent
Antoniou et al.

(10) Patent No.: US 6,949,361 B2
(45) Date of Patent: Sep. 27, 2005

(54) POLYNUCLEOTIDE

(75) Inventors: Michael Antoniou, Edgeware (GB); Robert L. Crombie, Barbridge (GB); Steven G. Williams, Crewe (GB)

(73) Assignee: M.L. Laboratories PLC, London (GB)

( * ) Notice: Subject to any disclaimer, the term of this patent is extended or adjusted under 35 U.S.C. 154(b) by 94 days.

(21) Appl. No.: 09/957,974

(22) Filed: Sep. 20, 2001

(65) Prior Publication Data

US 2002/0094967 A1 Jul. 18, 2002

Related U.S. Application Data

(60) Provisional application No. 60/252,048, filed on Nov. 20, 2000.

(30) Foreign Application Priority Data

Sep. 20, 2000 (GB) .............................. 0022995

(51) Int. Cl.$^7$ ................................ C12P 21/02
(52) U.S. Cl. ................... 435/69.1; 435/325; 435/320.1; 536/24.1
(58) Field of Search ........................ 514/44; 435/320.1, 435/325, 69.1; 536/24.1

(56) References Cited

PUBLICATIONS

Ng et al., Mol. Cell. Biol., vol. 5, 1985, pp. 2720–2732.*
Verma et al., Nature, vol. 389, 1997, pp. 239–242.*
Anderson, Nature, vol. 392 (suppl.), 1998, pp. 25–30.*
Juengst, Brit. Med. J., vol. 326, pp. 1410–1411.*
Antequera, F. & Bird, A., "Number of CpG islands and genes in human and mouse" *Proc. Natl. Acad. Sci. USA*, 1993, 90, 11995–11999.
Bell, A.C. & Felsenfield, G., "Stopped at the border: boundaries and insulators" *Curr. Opin. Genet. Dev.*,1999, 9, 191–198.
Bird et al., A fraction of the mouse genome that is derived from islands of nonmethylated, CpG–rich DNA, *Cell*, 1985, 40:91–99.
Dillon, N. & Grosveld, F., "Chromatin domains as potential units of eukaryotic gene function" *Curr. Opin. Genet. Dev.*, 1994, 4, 260–264.
Hammer, et al., "Production of transgenic rabbits, sheep and pigs by microinjection" *Nature*, 1985, 315:680–683.
Hicks, et al., "Functional genomics in mice by tagged sequence mutagenesis" *Nature Genetics*, 1997, 16, 338–344.
Kioussis, D. & Festenstein, R., "Locus control regions: overcoming heterochromatin–induced gene inactivation in mammals" *Curr. Opin. Genet. Dev.*,1997, 7, 614–619.
Needham, et al., "Further development of the locus control region/murine erthroleukemia expression system:high level expression and characterization of recombinant human calcitonin receptor" *Protein Expr. Purif.*, 1995, 6:124–131.
Sabbattini, P., Georgiou, A., Sinclaire, C. & Dillon, N., "Analysis of mice with single and multiple copies of transgenes reveals a novel arrangement for the λ5–V–preBI locus control region" *Mol. Cell. Biol*, 1999,19, 671–679.
Tazi, J. & Bird, A., "Alternative chromatin structure at CpG islands",*Cell* 60,1990, 909–920.

* cited by examiner

*Primary Examiner*—James Ketter
(74) *Attorney, Agent, or Firm*—Cozen O'Connor, P.C.

(57) ABSTRACT

The present invention relates to a polynucleotide comprising a ubiquitous chromatin opening element (UCOE) that does not occur in nature. The present invention also relates to a vector comprising the polynucleotide sequence, a host cell comprising the vector and use of the polynucleotide, vector or host cell in therapy, or for in vitro protein expression applications.

50 Claims, 26 Drawing Sheets

```
catggcacct gtattgtact cttatcagtc attatatgga ctttaacttc gtatcgtgga    60
cataacatga gaatagtcag taatatacct gaaattgaag cccagatatt atttgggctc   120
ctccataaga ctgtgagcat ctgaccactg gggtctataa taaacccgag gaggtattct   180
gacactcgta gactggtgac gagtgttgct tcccattata tccctgttat caagcacaag   240
gtcaggcaca ctcacaacga agggtaatat aggacaata gttcgtgttc cagtccgtgt    300
gagtaagact caaaacatgt tttggaatgt atgactggta tgaactacaa ctcattctga   360
gttttgtaca aaaccttaca tactgaccat acttgatgtt accagtaagc tgatgttttc   420
attttgagtc tataaatcta attttgtggt tggtcattcg actacaaaag taaaactcag   480
atatttagat taaaacacca ggttttgtgt atggctcaag gctcaaattg taaaatttaa   540
tattatgtga ccaaaacaca taccgagttc cgagtttaac attttaaatt ataatacact   600
ccaaagaaag ttatacccag aacctcaatt tcctcaccct caaaatgggg ggtttctttc   660
aatatgggtc ttggagttaa aggagtggaa gttttacccc cagtttctca ctcattggtc   720
tgctgtcacg attttaatga gctcatgcac gtcaaagagt gagtaaccag acgacagtgc   780
taaaattact cgagtacgtg aaacagccct ttatataagg taagtgctgg ataaatgttg   840
gctactataa tttgtcggga aatatattcc attcacgacc tatttacaac cgatgatatt   900
taaaataagc ctctaagata cttggtcagc acaagtacta cccaagagta attttattcg   960
gagattctat gaaccagtcg tgttcatgat gggttctcat tgcactgtaa gtaaactgac  1020
aaaattgtgt atctaaaact ggccagatga acgtgacatt catttgactg ttttaacaca  1080
tagatttgat ccggtctact aagagaaact tttaaggggc ccttctgcgt gcccgacact  1140
gtgctaggca ttctctttga aaattccccg ggaagacgca cgggctgtga cacgatccgt  1200
ctcacactat cccgacccga gaaaccgatc tgcgacccag aggaacttac gagtgtgata  1260
gggctgggct ctttggctag acgctgggtc tccttgaatg caagcctcca gcatcttgtg  1320
cagccctact catgggacca tctggatacc gttcggaggt cgtagaacac gtcgggatga  1380
gtaccctggt agacctatgg caccctttgtc tttacaggga gcagaacaca cctcttatgt  1440
gtcagaaaac gtgggaacag aaatgtccct cgtcttgtgt ggagaataca cagtcttttg  1500
aaagtccagg aagtatattt ttacctgagg caatatctga aaattgtatg tttcaggtcc  1560
ttcatataaa aatggactcc gttatagact tttaacatac ctacagcctc caaagtgagt  1620
cttcctctca gtacctctct tctaggcaca gatgtcggag gtttcactca gaaggagagt  1680
catggagaga agatccgtgt tggagcccct tcttccaagt attatgttta accacttaat  1740
gaatgaagtc acctcgggaa agaaggttca taatacaaat tggtgaatta cttacttcag  1800
ctgaaactgc ttaccatgc tccctataat ctctgagtaa tcttcctttt gactttgacg  1860
aatgggtacg agggatatta gagactcatt agaaggaaaa ccacaacctc aggcataatc  1920
```

FIG. 2-1

```
tcatcttctg tttctattac aatttcaaat ggtgttggag tccgtattag agtagaagac   1980
aaagataatg ttaaagttta tctggaaaaa ggaagttgtg gtctggaatt atatggtcca   2040
gatgatctga agacctttt ccttcaacac cagaccttaa tataccaggt ctactagact   2100
aacaaaaagg acagcactat tagtaatcat ttagttttga agacagtcta ttgttttcc    2160
tgtcgtgata atcattagta aatcaaaact tctgtcagat ataatttgct gtctctaaag   2220
tactatattc cctatagttc tggcatttta tattaaacga cagagatttc atgatataag   2280
ggatatcaag accgtaaaat gataaagggt cataaattaa atgcctatat ggtgacatta   2340
ttcagtgatt ctatttccca gtatttaatt tacggatata ccactgtaat aagtcactaa   2400
cagacttcac agccttttt tttttttac aaggtgttc caggcatgaa gtctgaagtg     2460
tcggaaaaaa aaaaaaatg tttccacaag gtccgtactt aaatttaaa gtactatacc    2520
tttcctaatt ttacctttaa agttgtcctg tttaaaattt catgatatgg aaaggattaa   2580
aatggaaatt tcaacaggac gaaatatctg ggttgacaaa ggcgatgaaa ctgaactgag   2640
acttaaaaaa ctttatagac ccaactgttt ccgctacttt gacttgactc tgaatttttt   2700
aagattaccc acctggttgt gcacaagcct gcttatgtcc caatctccag ttctaatggg   2760
tggaccaaca cgtgttcgga cgaatacagg gttagaggtc tctagggtct gatgctcctt   2820
gctgcagtaa tatgctttgt ggcatctgga agatcccaga ctacgaggaa cgacgtcatt   2880
atacgaaaca ccgtagacct gcacgttttg gggcctaaac agccacaaac cctgcagaga   2940
tgagcaccag cgtgcaaaac cccggatttg tcggtgtttg ggacgtctct actcgtggtc   3000
acttaagctg gagacacact gattctcctg tttctggggg aggattctca tgaattcgac   3060
ctctgtgtga ctaagaggac aaagaccccc tcctaagagt gaaggtggct catatgagta   3120
aaaatcgttt ttcctgggta gttgattcct cttccaccga gtatactcat ttttagcaaa   3180
aaggacccat caactaagga aaaactaaa aagaataca gagaaaagtt ttatcttcaa    3240
acaaaacagc tttttgattt tttcttatgt ctcttttcaa aatagaagtt tgttttgtcg   3300
aattcacata ttttatcctc tgcacgtaaa actgaaaata acaacaacaa ttaagtgtat   3360
aaaataggag acgtgcattt tgacttttat tgttgttgtt aaaagaaatg aaagttttg    3420
ctttcaggaa taagctttta aaatccagaa ttttctttac tttcaaaaac gaaagtcctt   3480
attcgaaaat tttaggtctt actagatttc gtccggtaca cgcaactgag ttgcctccta   3540
gaggtggttt tgatctaaag caggccatgt gcgttgactc aacggaggat ctccaccaaa   3600
gagttaatca aattaataag actgatcgtt aagaacgact gccaaaaata ctcaattagt   3660
ttaattattc tgactagcaa ttcttgctga cggtttttat cgaaaaagct actgggatcc   3720
```

FIG. 2-2

```
atctttccaa gacaatttct attatctgaa gcttttcga tgacsctagg tagaaaggtt   3780
                                    KpnI
ctgttaaaga taatagactt ttaacaccat acctggtacc cactgattaa aagctggggg   3840
ttaccaatgc aattgtggta tggaccatgg gtgactaatt ttcgaccccc aatggttacg   3900
gcgtgggcac agttagaagc ttatgtagca aaaatgagca catcctggaa cgcacccgtg   3960
tcaatcttcg aatacatcgt ttttactcgt gtaggacctt gggcccggga gaaggtgctc   4020
ctggggcagc gcggagaggg agctctgagg cccgggccct cttccacgag gacsccgtcg   4080
cgcctctccc tcgagactcc ctggggcggc agcggtgctt gccgccgtcc ccctggtcgc   4140
tcccggaatt gaccccgccg tcgccacgaa cggcggcagg gggaccagcg agggccttaa   4200
aacgccgcgc acgcgtcgga ggcatggccc cgtcccgacc ccgtttggcg ttgcggcgcg   4260
tgcgcagcct ccgtaccggg gcaggctgg ggcaaaccgc gctcacctcg caggccggca   4320
cagcacggct gctcgcggca gcagaagagg cgagtggagc gtccggccgt gtcgtgccga   4380
cgagcgccgt cgtcttctcc aagatgcagc ggtggaaggc gtccgggcgg ccaggcagcg   4440
gcgcatacac ttctacgtcg ccaccttccg caggcccgcc ggtccgtcgc cgcgtatgtg   4500
ctgcagcagg aaggagagcg ggcggccgca cagctcgcag gccagggcct gacgtcgtcc   4560
ttcctctcgc ccgccggcgt gtcgagcgtc cggtcccgga ggggccccgg cagcccggcc   4620
gcgcccagcc atgccggccg cccgcccacc ccccggggcc gtcgggccgg cgcgggtcgg   4680
tacggccggc gggcgggtgg ttgctgggga actgctcgct gcgcagtcgc cacgccggcg   4740
ccgactcggc aacgaccsct tgacgagcga cgcgtcagcg gtgcggccgc ggctgagccg   4800
gaagcccagc tccacaggcc tggccccggc ggcagccatg cggggcgcgg cttcgggtcg   4860
aggtgtccgg accggggccg ccgtcggtac gccccgcgcc gctggcgtgg ggcgcagcc   4920
acagctgggt cggaaggcgg aaatcgggcg cgaccgcacc ccgcgtcggg tgtcgaccca   4980
gccttccgcc tttagcccgc ccgggccgga aggcaagagg cgggcacctt tccggaggac   5040
aggaggcgga ggcccggcct tccgttctcc gcccgtggaa aggcctcctg tcctccgcct   5100
aacgcgtctg acgggagcgg ttgcaggacc aatgcgaggg aacggggcag ttgcgcagac   5160
tgccctcgcc aacgtcctgg ttacgctccc ttgccccgtc aggaaacctc tcggcatcag   5220
ccccgcccct ggcgcctctg cctccgagcc tcctttggag agccgtagtc ggggcggga   5280
ccgcggagac ggaggctcgg gctttcctgg tgcctccggg tgtctggga tggttctggt   5340
ctttgggaga cgaaaggacc acggaggccc acgagaccct accaagacca gaaaccctct   5400
gtggcagctg gtgacggcgc tccgctcacc tctgcacatg tcttgctgtg caccgtcgac   5460
cactgccgcg aggcgagtgg agacgtgtac agaacgacac ggcctgcggg tggccgccag   5520
ggaggcagag ccctcccgca aaccttccct ccggacgccc accggcggtc cctccgtctc   5580
gggagggcgt ttggaaggga gctggtgtcc acctcagggt gtgggaaacc tgtgcgctgg   5640
```

FIG. 2-3

| | | | | | |
|---|---|---|---|---|---|
| ccgagtgcta | cgaccacagg | tggagtccca | caccctttgg | acacgcgacc | ggctcacgat 5700 |
| accaagagta | ggcagtgaaa | gacaaatgaa | ggttgaacag | gtaaagtgag | tggttctcat 5760 |
| ccgtcacttt | ctgtttactt | ccaacttgtc | catttcactc | gaccctacag | cggaaaccaa 5820 |
| gaatcctgtg | tgcctgagag | taatgaagaa | ctgggatgtc | gcctttggtt | cttaggacac 5880 |
| acggactctc | attacttctt | gcctctgcag | aagagtcttt | tctgtcagtc | ttaaggtctc 5940 |
| tgttttaatg | cggagacgtc | ttctcagaaa | agacagtcag | aattccagag | acaaaattac 6000 |
| ttagtgctgg | cttgctgtac | ctgaattcca | agggaggagt | gtataatgag | aatcacgacc 6060 |
| gaacgacatg | gacttaaggt | tccctcctca | catattactc | gcatggccaa | ccccacttc 6120 |
| ccatcattgc | ctgaactagt | ttttcaggtt | cgtaccggtt | gggggtgaag | ggtagtaacg 6180 |
| | | | KpnI | | |
| gacttgatca | aaaagtccaa | aacttcagaa | tgcccttggt | accgcgggcc | ccctctgtgg 6240 |
| tcccacgcca | ttgaagtctt | acgggaacca | tggcgccgg | gggagacacc | agggtgcggt 6300 |
| ctgatcgctg | catgcccacc | acctgggtac | acacagtctg | tgattcccgg | gactagcgac 6360 |
| gtacgggtgg | tggacccatg | tgtgtcagac | actaagggcc | agcagaacgg | accctgccca 6420 |
| ccggtcttg | tgtgctactc | agtggacaga | tcgtcttgcc | tgggacgggt | gggccagaac 6480 |
| acacgatgag | tcacctgtct | cccaaggcaa | gaaagggtga | caaggacagg | gtcttcccag 6540 |
| gctggctttg | gggttccgtt | ctttcccact | gttcctgtcc | cagaagggtc | cgaccgaaac 6600 |
| agttcctagc | accgccccgc | ccccaatcct | ctgtggcaca | tggagtcttg | tcaaggatcg 6660 |
| tggcggggcg | ggggttagga | gacaccgtgt | acctcagaac | gtcccagag | tccccagcg 6720 |
| gcctccagat | ggtctgggag | ggcagttcag | cagggggtctc | aggggggtcgc | cggaggtcta 6780 |
| ccagaccctc | ccgtcaagtc | ctgtggctgc | gcatagcaga | catacaacgg | acggtgggcc 6840 |
| cagacccagg | gacaccgacg | cgtatcgtct | gtatgttgcc | tgccaccgg | gtctgggtcc 6900 |
| ctgtgtagac | ccagcccccc | cgccccgcag | tgcctaggtc | acccactaac | gacacatctg 6960 |
| ggtcgggggg | gcggggcgtc | acggatccag | tgggtgattg | gcccaggcc | tggtcttggc 7020 |
| tgggcgtgac | tgttaccctc | aaaagcaggc | cggggtccgg | accagaaccg | accgcactg 7080 |
| acaatgggag | ttttcgtccg | agctccaggg | taaaaggtgc | cctgcctgt | agagcccact 7140 |
| tccttcccag | tcgaggtccc | attttccacg | ggacgggaca | tctcgggtga | aggaagggtc 7200 |
| ggctgcggct | gggtaggttt | gtagccttca | tcacgggcca | cctccagcca | ccgacgccga 7260 |
| cccatccaaa | catcggaagt | agtgcccggt | ggaggtcggt | ctggacagct | ggcccctgcc 7320 |
| ctgtcctggg | gagtgtggtc | ctgcgactct | gacctggcga | ccggggacgg | gacaggaccc 7380 |
| ctcacaccag | gacgctgaga | aatggccgca | agccacctga | ctccccaac | accacactct 7440 |

FIG. 2-4

```
acctctcaag ttaccggcgt tcggtggact gagggggttg tggtgtgaga tggagagttc  7500
cccaggtctc tccctagtga cccacccagc acatttagct agctgagccc gggtccagag  7560
agggatcact gggtgggtcg tgtaaatcga tcgactcggg cacagccaga ggtcctcagg  7620
ccctgctttc agggcagttg ctctgaagtc gtgtcggtct ccaggagtcc gggacgaaag  7680
tcccgtcaac gagacttcag ggcaagggg agtgactgcc tggccactcc atgccctca   7740
agagctcctt ccgttccccc tcactgacgg accggtgagg tacgggaggt tctcgaggaa  7800
ctgcaggagc gtacagaacc cagggccctg gcacccgtgc agaccctggc gacgtcctcg  7860
catgtcttgg gtcccgggac cgtgggcacg tctgggaccg ccacccacc tgggcgctca   7920
gtgcccaaga gatgtccaca cctaggatgt ggtggggtgg acccgcgagt cacgggttct  7980
ctacaggtgt ggatcctaca cccgcggtgg gtgggggcc cgagagacgg gcaggccggg   8040
ggcaggcctg gggcgccacc cacccccgg gctctctgcc cgtccgccc ccgtccggac    8100
gccatgcggg gccgaaccgg gcactgccca gcgtgggcg cggggccac cggtacgcc     8160
cggcttggcc cgtgacgggt cgcacccgc gccccggtg ggcgcgcgcc cccagccccc    8220
gggcccagca ccccaaggcg gccaacgcca ccgcgcgcgg gggtcggggg cccgggtcgt   8280
ggggttccgc cggttgcggt aaactctccc tcctcctctt cctcaatctc gtctcgctc   8340
ttttttttt tttgagaggg aggaggagaa ggagttagag cgagagcgag aaaaaaaaaa   8400
tcgcaaaagg aggggagagg gggtaaaaaa atgctgcact gtgcggcgaa agcgttttcc  8460
tcccctctcc cccattttt tacgacgtga cacgccgctt gccggtgagt gagcggcgcg   8520
gggccaatca gcgtgcgccg ttccgaaagt cggccactca ctcgccgcgc ccggttagt   8580
cgcacgcggc aaggctttca tgccttttat ggctcgagcg gccgcggcgg cgccctataa  8640
aacccagcgg acggaaaata ccgagctcgc cggcgccgcc gcgggatatt ttgggtcgcc  8700
cgcgacgcgc caccaccgcc gagaccgcgt ccgcccgcga gcacagagcc gcgctgcgcg  8760
gtggtggcgg ctctggcgca ggcgggcgct cgtgtctcgg tcgcctttgc cgatccgccg  8820
cccgtccaca cccgcgcca ggtaagcccg agcggaaacg gctaggcggc gggcaggtgt   8880
gggcggcggt ccattcgggc gccagccgac cggggcatgc ggccgcggcc cttcgcccgt  8940
gcagagccgc cggtcggctg gccccgtacg ccggcgccgg gaagcgggca cgtctcggcg  9000
cgtctgggcc gcagcggggg gcgcatgggg cggaaccgga ccgccgtggg gcagacccgg  9060
cgtcgccccc cgcgtacccc gccttggcct ggcggcaccc gggcgcggga gaagccctg   9120
ggcctccgga gatgggggac acccacgcc ccgcgccct cttcggggac ccggaggcct    9180
ctacccctg tggggtgcgg agttcgcagg cgcgaggccg cgctcgggcg ggcgcgctcc   9240
gggggtgccg tcaagcgtcc gcgctccggc gcgagcccgc ccgcgcgagg ccccccacggc 9300
```

FIG. 2-5

```
ctctcgggge  gggggcaacc  ggcggggtct  ttgtctgagc  cgggctcttg  gagagcccg   9360
ccccgttgg   ccgccccaga  aacagactcg  gcccgagaac  ccaatgggga  tcgcacggtg  9420
ggcgcggcgt  agccccgtc   aggcccggtg  ggttaccct   agcgtgccac  ccgcgccgca  9480
tcggggcag   tccgggccac  ggggctgggg  cgccatgcgc  gtgcgcgctg  gtcctttggg  9540
cgctaactgc  ccccgacccc  gcggtacgcg  cacgcgcgac  caggaaaccc  gcgattgacg  9600
gtgcgcgctg  ggaattggcg  ctaattgcgc  gtgcgcgctg  ggactcaatg  cacgcgcgac  9660
ccttaaccgc  gattaacgcg  cacgcgcgac  cctgagttac  gcgctaatcg  cgcgtgcgtt  9720
ctggggcccg  ggcgcttgcg  ccacttcctg  cgcgattagc  gcgcacgcaa  gacccgggc   9780
ccgcgaacgc  ggtgaaggac  cccgagccgc  tggcgcccga  gggtgtggcc  gctgcgtgcg  9840
cgcgcgcgac  gggctcggcg  accgcgggct  cccacaccgg  cgacgcacgc  gcgcgcgctg  9900
ccggtcgctg  tttgaaccgg  gcggaggcgg  ggctggcgcc  cggttgggag  ggccagcgac  9960
aaacttggcc  cgcctccgcc  ccgaccgcgg  gccaaccctc  ggggttgggg  cctggcttcc  10020
tgccgcgcgc  cgcggggacg  cctccgacca  cccaacccc   ggaccgaagg  acggcgcgcg  10080
gcgcccctgc  ggaggctggt  gtgtttgcct  tttatggtaa  taacgcggcc  ggcccggctt  10140
cctttgtccc  cacaaacgga  aaataccatt  attgcgccgg  ccgggccgaa  ggaaacaggg  10200
caatctgggc  gcgcgccggc  gccccctggc  ggcctaagga  ctcggcgcgc  gttagacccg  10260
cgcgcggccg  cggggaccg   ccggattcct  gagccgcgcg  cggaagtggc  cagggcgggg  10320
gcgacttcgg  ctcacagcgc  gccggctat   gcttcaccg   gtcccgcccc  cgctgaagcc  10380
gagtgtcgcg  cgggccgata  tctcgcagct  caccatgccg  gtcgccacca  tgagagcgtc  10440
gagtggtacg  gccagcggtg  gtac                                            10464
```

FIG. 2-6

```
aagcttactt gattggccat gtggcaagcg acaggcacaa aacaattttc ttcgaatgaa      60
ctaaccggta caccgttcgc tgtccgtgtt ttgttaaaag caagtcaata ggaaaaacct    120
cagagctgaa atctttatat gctgtactac gttcagttat ccttttttgga gtctcgactt    180
tagaaatata cgacatgatg acagctgtat tctgggcact tatgaatgtt aaggaaacct    240
gtcttaaaag tgtcgacata agacccgtga atacttacaa ttcctttgga cagaattttc    300
ttaactaggt taaaaaacct caaacgagag aaagtgatat ccaggaccaa aattgatcca    360
atttttgga gtttgctctc tttcactata ggtcctggtt ctgctacaaa cgcataatgc    420
aaactaaaaa gtcacacgta attttcaatc gacgatgttt gcgtattacg tttgatttt    480
cagtgtgcat taaaagttag aattattttt tgttcctagc aagcagcatt aattgctgct    540
ctcatcccag ttaataaaaa acaaggatcg ttcgtcgtaa ttaacgacga gagtagggtc    600
ttctacggag ctctccctcc attcgcatgc tcccaactcc taaaaagtag aagatgcctc    660
gagagggagg taagcgtacg agggttgagg atttttcatc tggtaaaacc cagttcagat    720
ttttttcct gtagttttca tgactcgtaa accatttttgg gtcaagtcta aaaaaagga    780
catcaaaagt actgagcatt aaattaaaga aaaaattaac tgaaatgatc aaactagctc    840
ctatgagaca tttaattct tttttaattg actttactag tttgatcgag gatactctgt    900
caaagcagtc ttttgaaatg gttacttgtc acgatagtta ttttcatttt gtttcgtcag    960
aaaactttac caatgaacag tgctatcaat aaaagtaaaa ttcagctagt ttttattctt   1020
aattgtcgtc agcacatagg ttatctctaa aagtcgatca aaataagaa ttaacagcag   1080
tcgtgtatcc aatagagatt actgaaatta cggataatgt acatttataa caagtttac   1140
aaatcactaa tgactttaat gcctattaca tgtaaatatt gttcaaaatg tttagtgatt   1200
caaaaagcaa aaactcatta cttacctcac aatttatcca aacttacccg gttttcgtt   1260
tttgagtaat gaatggagtg ttaaataggt ttgaatgggc atgtccacta tcgattttaa   1320
acaatgttat tttataaacg tgcttagggt tacaggtgat agctaaaatt tgttacaata   1380
aaatatttgc acgaatccca caagaaaaa taaccaggta gacccccttc gcttgagacc   1440
ttatgcttat gtttcttttt attggtccat ctggggggaag cgaactctgg aatacgaata   1500
caatgtaatg ttcaaccaag attgcaaaca aaatgagaaa agtaacaaag gttacattac   1560
aagttggttc taacgtttgt tttactcttt tcattgtttc ttcaaataca gagcggccca   1620
ggcccaaaac agttttgcac atcaatccat aagtttatgt ctcgccgggt ccgggttttg   1680
tcaaaacgtg tagttaggta acgcattaca ggaaggagcc tctgaagcca tgttttaatc   1740
gaagtataac tgcgtaatgt ccttcctcgg agacttcggt acaaaattag cttcatattg   1800
```

FIG. 7-1

```
                                                  NcoI
taaggacaaa atcgttattt cactttcctc gtaatcatct ataaaggtcc attcctgttt   1860
                                                  NcoI
tagcaataaa gtgaaaggag cattagtaga tatttccagg atggatctgt cccgtaaggg   1920
ttaaacttct cagtaacaac attacttaaa tacctagaca gggcattccc aatttgaaga   1980
gtcattgttg taatgaattt atgagtcagc tctacaactt aaacggaatc cttaagaaca   2040
gtaaaggatt tactcagtcg agatgttgaa tttgccttag gaattcttgt catttcctaa   2100
ctgacgcgaa tatccctccc ccgcccagaa aaccaccttc gtccctgccc gactgcgctt   2160
atagggaggg ggcgggtctt ttggtggaag cagggacggg ctcgtggccg atggcttcca   2220
atttatgttt attttgccgc ggttcatctg gagcaccggc taccgaaggt taaatacaaa   2280
                                              PstI
taaaacggcg ccaagtagac ttgttttact gactgcagac ccagataaaa ccgttactca   2340
aaggaaaaaa agcaaaatga ctgacgtctg ggtctatttt ggcaatgagt ttccttttt    2400
aagacaggaa aaacataaaa tggtttcttt gtcctacggc tcgcattgaa ttctgtcctt   2460
tttgtatttt accaaagaaa caggatgccg agcgtaactt cccggcccga cgccctgggt   2520
ggtgatatct tctctgaaac cgggcccgca gggccgggct gcgggaccca ccactataga   2580
agagactttg gcccggcgt aacccggagc acccccctc cccgctcttc ggtgtggctt    2640
ccgaacgcaa ttgggcctcg tggggggag gggcgagaag ccacaccgaa ggcttgcgtt    2700
tggcgccatt tcatcgaggg gaaggctgag cgcctttaat gaggtgcgca accgcggtaa   2760
agtagctccc cttccgactc gcggaaatta ctccacgcgt ggactctaaa gatccaagct   2820
cacaaaacac tccaaatcca cctcgaaacg cctgagattt ctaggttcga gtgttttgtg   2880
aggtttaggt ggagctttgc atatgaaaac agcccgagaa gaaaaaaaaa atagttaacc   2940
acttctactt tatactttg tcgggctctt ctttttttt tatcaattgg tgaagatgaa    3000
cttgatagag aaagcacact aagaaaataa aagagttata aggaaaacgc gaactatctc   3060
tttcgtgtga ttctttatt ttctcaatat tccttttgcg tgagaggaag gcgagccatg    3120
                                 SmaI
aaaatggcgg ccgccaaatc ggttcccggg actctccttc cgctcggtac ttttaccgcc   3180
ggcggtttag ccaagggccc agagaggggg aggggaagct ccgcagcctc gctcacgagg   3240
acctgctgcc tctctcccc tcccttcga ggcgtcggag cgagtgctcc tggacgacgg    3300
cgccgaaacg ctcgccgagg agacgccgtg gccccgaag cagcgtgctt gcggctttgc    3360
gagcggctcc tctgcggcac cgggggcttc gtcgcacgaa tagaaaggga ataagaattc   3420
ccgcctccgc gcccacttt cacccagcg atctttcct tattcttaag ggcggaggcg     3480
cggggtgaaa gtgggtcgc gggcagcgtc cgccatgtga aagctcccca tcccccaccc   3540
ccagtgaagg cccgtcgcag gcggtacact ttcgaggggt agggggtggg ggtcacttcc   3600
```

FIG. 7-2

```
gaaatggcgc cgggaggctg agggtgggga agctgtttgt acgctcaggc ctttaccgcg   3660
gccctccgac tcccacccct tcgacaaaca tgcgagtccg ctccgctcaa gacccgttc    3720
ataaaccta  agcccactg  ctactgaatt  gaggcgagtt ctgggcaag  tatttggaat  3780
tcggggtgac gatgacttaa ggtccgattt cctgcctctc tccacggag  gcggctggcc   3840
gacttccact ccaggctaaa ggacggagag agggtgcctc cgccgaccgg ctgaaggtga   3900
gaggcgccaa cggcctcgcc atgcccttt  caataactca ttgatttcaa ctccgcggtt   3960
gccggagcgg tacgggaaaa gttattgagt aactaaagtt acccgttacc tccatcgcgg   4020
actcagtcgc ttcagcccga tttcccgcag tgggcaatgg aggtagcgcc tgagtcagcg   4080
                                          BglII
aagtcgggct aaagggcgtc ccgagcgaga tgagagagat ctccgcggac gaacacgaac    4140
cggactcgtc ggctcgctct actctctcta gaggcgcctg cttgtgcttg gcctgagcag   4200
                              XhoI
ctggcgctgt agtgagaact gccgctgctc gagaaacaac tctgcgagga gaccgcgaca   4260
tcactcttga cggcgacgag ctctttgttg agacgctcct gcacctccgc acgggacccg   4320
gcgctgctgc tactgccgct agagccgctg cgtggaggcg tgccctgggc cgcgacgcg    4380
atgacggcga tctcggcgac ccgccgcttt tctagaacct tcccccccac taacgcgtct   4440
tccgctacgt ggcggcgaaa agatcttgga aggggggtg  attgcgcaga aggcgatgca   4500
caggccgtcg cgtaaacgcc ctatccgccg ccaatggcgg gaaggctcta gtccggcagc   4560
gcatttgcgg gataggcggc ggttaccgcc cttccgagat cgccccacct tacgccaaat   4620
gcgtactcct cccacccttg cggccagaga gcgggtgga  atgcggttta cgcatgagga   4680
gggtgggaac gccggtctct cagtacccga cgttacttcc gtaaatgcgc tcaatgaatt   4740
gcggaaggct gtcatgggct gcaatgaagg catttacgcg agttacttaa cgccttccga   4800
agagtcctgc tagttactac ctcttggaat agggtcccgg ccctgcctt  tctcaggacg   4860
atcaatgatg gagaaccta  tcccagggcc ggggacggaa ggcgaaggca ggtgagaaac   4920
gtcgcgcagt ttgaaattaa cgccgacggg ccgcttccgt ccactctttg cagcgcgtca   4980
aactttaatt gcggctgccc agggcttaa  tccgcagcct ggagatccag ccccctcaac   5040
  SmaI
ccgggaggtg tccccgaatt aggcgtcgga cctctaggtc gggggagttg ggccctccac   5100
    PstI
gtccctgcag ttacgccaat gataacccc  gccagaaaaa tcttagtagc cagggacgtc   5160
aatgcggtta ctattggggg cggtcttttt agaatcatcg cttccctttt tgttttccgt   5220
gccccaactc ggcggattga ctcggcccct gaagggaaaa acaaaaggca cggggttgag   5280
ccgcctaact gagccgggga tccggaaaca cccgaatcaa cttctagtca aattattgtt   5340
cacgccgcaa aggcctttgt gggcttagtt gaagatcagt ttaataacaa gtgcggcgtt   5400
```

FIG. 7-3

```
tgacccaccc ctggcccgcg tctgtggaac tgaccoctgg tgtacaggag actgggtggg    5460
gaccgggcgc agacaccttg actggggacc acatgtcctc agttcgctgc tgaaagtggt    5520
cccaaagggg tactagtttt taagctccca tcaagcgacg actttcacca gggtttcccc    5580
atgatcaaaa attcgagggt actccccctc cccagcgtc tggaggattc cacaccctcg     5640
caccggcggg tgaggggag ggggtcgcag acctcctaag gtgtgggagc gtggccgcc      5700
cgaggaagtg ggcggagtcc ggttttggcg ccagccgctg aggctgccaa gctccttcac    5760
ccgcctcagg ccaaaaccgc ggtcggcgac tccgacggtt gcagaaaagc caccgctgag    5820
gagactccgg tcactgtcct cgcoccgcct cgtcttttcg gtggcgactc ctctgaggcc    5880
agtgacagga gcgggcgga cccccttccc tccccttggg gaccaccggg cgccacgccg     5940
cgaacggtaa gggggaaggg aggggaaccc ctggtggccc gcggtgcggc gcttgccatt    6000
gtgccgcggt cgtcggcgcc tccgccctcc ccctagggcc ccaattccca cacggcgcca    6060
gcagccgcgg aggcgggagg gggatcccgg ggttaagggt gcgggcgcgg cgccggcccc    6120
tcccccgcc gcgcgcgcgc ccgctgcccc cgcccgcgcc gcggccgggg agggggcgg      6180
cgcgcgcgcg ggcgacgggg gccttcgtg gccgcccggc gtgggcggtg ccacccctcc     6240
ccccggcggc cgggaagcac cggcgggccg caccgccac ggtggggagg ggggccgccg     6300
cccgcgcgca gctcccggct ccctcccct tcggatgtgg cttgagctgt gggcgcgcgt     6360
cgagggccga gggaggggga agcctacacc gaactcgaca aggcgcggag ggccggagac    6420
       PstI
gctgcagacc cgcgacccgg agcagctcgg tccgcgcctc ccggcctctg cgacgtctgg    6480
gcgctgggcc tcgtcgagcc aggcggtgaa gtcggtgget ttccttctct ctagctctcg    6540
ctcgctggtg tccgccactt cagccaccga aaggaagaga gatcgagagc gagcgaccac    6600
                                SmaI
gtgcttcaga tgccacacgc gtcccggggg cccggttctc cgctcccctc cacgaagtct    6660
acggtgtgcg cagggcaccc gggccaagag gcgaggggag ccctccctt ctgccggac     6720
cccgcgccgg gagctgcggg aaggagtgga gggaggggaa gagcggcctg gggcgcggcc    6780
ctcgacgccc ttcctcacct gggtcgggcg gtggcctcgc ggctggcctg gcgcgcggcc    6840
agcccggtag cccagcccgc caccggagcg ccgaccggac cgcgcgccgg tcgggcaatc    6900
                                   XhoI
ttagtggggg gactgctctg ccctcgaggg ggtagggagc tgtggcgacg aatcaccccc    6960
ctgacgagac gggagctccc ccatccctcg acaccgctgc gttgcccat ttcgagacaa     7020
agcgcatttc ccctcccct cccccaccg caacggggta aagctctgtt tcgcgtaaag      7080
ggggagggga ggggtgggc cgttccggcg gaggcgcccc ctcccccagc gccacgcggg     7140
gctgggtcga gcaaggccgc ctccgcgggg gagggggtcg cggtgcgccc cgacccagct    7200
```

FIG. 7-4

```
gacttgggcc tcccggaggg cggcgcgtgg tcccgcgtcc gcgagcctgg ctgaacccgg   7260
agggcctccc gccgcgcacc agggcgcagg cgctcggacc cggcgcgcgg ccggctgtcc   7320
cgaggctgcg gcgaccgcca gttaacgtgg gccgcgcgcc ggccgacagg gctccgacgc   7380
cgctggcggt caattgcacc ccgcgcgggg gtaggcgcgt gcggtgtggc gcagtgccct   7440
tgagcccccg ggcgcgcccc catccgcgca cgccacaccg cgtcacggga actcgggggc   7500
tgccgcggcc tttgtttctc cccgcggatg cgctgaccac gaggcccgcg acggcgccgg   7560
                                                  SmaI
aaacaaagag gggcgcctac gcgactggtg ctccgggcgc ctcccgggtg ggggcgggca   7620
cccgcgctta ggcctctgga cgccgggctt gagggccoac ccccgcccgt gggcgcgaat   7680
ccggagacct gcggcccgaa cagcggcggg ggtcgggagc gggtgtttgc aagaggtgat   7740
tcttttttca gtcgccgccc ccagccctcg cccacaaacg ttctccacta agaaaaaagt   7800
aagtgtcacg aaacggggtt gaagcatctt aagttttttc cttttgttat ttcacagtgc   7860
tttgccccaa cttcgtagaa ttcaaaaaag gaaaacaata ttaattaccg attggaaaga   7920
gggagggttt ctgagcagaa accaagttgg aattaatggc taacctttct ccctcccaaa   7980
gactcgtctt tggttcaacc gattgcagaa cagagaagat tcacagtgct ttaccgttgt   8040
gagttgtttg ctaacgtctt gtctcttcta agtgtcacga aatggcaaca ctcaacaaac   8100
ggtaatcgtg cctggtttta aaccgaaagg attgtccttt aaaaatggaa ccattagcac   8160
ggaccaaaat ttggctttcc taacaggaaa ttttacctt catggacttt attataaatg    8220
ggacttagat tggaaaagac attggtcccc gtacctgaaa taatatttac cctgaatcta   8280
                                                         KpnI
acctttctg taaccagggg tattttaagc catgtgaagc tgttttaggt accgcgggcc    8340
ccctctgtgg ataaaattcg gtacacttcg acaaaatcca tggcgcccgg gggagacacc   8400
tcccacgcca ctgatcgctg catgcccacc acctgggtac acacagtctg agggtgcggt   8460
gactagcgac gtacggggtgg tggacccatg tgtgtcagac tgattcccgg agcagaacgg   8520
accctgccca cccggtcttg tgtgctactc actaagggcc tcgtcttgcc tgggacgggt   8580
gggccagaac acacgatgag agtggacaga cccaaggcaa gaaagggtga caaggacagg   8640
gtcttcccag tcacctgtct gggttccgtt ctttcccact gttcctgtcc cagaagggtc   8700
gctggctttg agttcctagc accgcccgc cccaatcct ctgtggcaca cgaccgaaac    8760
tcaaggatcg tggcggggcg ggggttagga gacaccgtgt tggagtcttg gtcccagag   8820
tcccccagcg gcctccagat ggtctgggag acctcagaac cagggtctc aggggtcgc    8880
cggaggtcta ccagaccctc ggcagttcag ctgtggctgc gcatagcaga catacaacgg   8940
acggtgggcc ccgtcaagtc gacaccgacg cgtatcgtct gtatgttgcc tgccaccgg   9000
```

FIG. 7-5

```
cagacccagg ctgtgtagac ccagccccc cgcccgcag tgcctaggtc gtctgggtcc   9060
gacacatctg ggtcgggggg gcggggcgtc acggatccag acccactaac gcccaggcc   9120
tggtcttggc tgggcgtgac tgttaccctc tgggtgattg cggggtccgg accagaaccg  9180
acccgcactg acaatgggag aaaagcaggc agctccaggg taaaaggtgc cctgccctgt   9240
agagcccact ttttcgtccg tcgaggtccc attttccacg ggacgggaca tctcgggtga   9300
tccttcccag ggctgcggct gggtaggttt gtagccttca tcacgggcca aggaagggtc   9360
ccgacgccga cccatccaaa catcggaagt agtgccggt cctccagcca ctggaccgct   9420
ggcccctgcc ctgtcctggg gagtgtggtc ggaggtcggt gacctggcga ccggggacgg   9480
gacaggaccc ctcacaccag ctgcgactct aatggccgca agccacctga ctcccccaac   9540
accacactct gacgctgaga ttaccggcgt tcggtggact gaggggttg tggtgtgaga   9600
                                                      NheI
acctctcaag cccaggtctc tccctagtga cccaccagc acatttagct tggagagttc   9660
                                                      NheI
gggtccagag agggatcact gggtgggtcg tgtaaatcga agctgagccc cacagccaga   9720
ggtcctcagg ccctgctttc agggcagttg tcgactcggg gtgtcggtct ccaggagtcc   9780
gggacgaaag tcccgtcaac ctctgaagtc ggcaaggggg agtgactgcc tggccactcc   9840
atgccctcca gagacttcag ccgttccccc tcactgacgg accggtgagg tacgggaggt   9900
           PstI
agagctcctt ctgcaggagc gtacagaacc cagggccctg gcaccgtgc tctcgaggaa   9960
gacgtcctcg catgtcttgg gtcccgggac cgtgggcacg agaccctggc ccaccccacc  10020
tgggcgctca gtgcccaaga gatgtccaca tctgggaccg ggtggggtgg acccgcgagt  10080
cacggttct ctacaggtgt cctaggatgt cccgcggtgg gtggggggcc cgagagacgg  10140
gcaggcggg ggatcctaca gggcgccacc caccccgg gctctctgcc cgtccggcc   10200
ggcaggcctg gccatgcggg gccgaaccgg gcactgccca gcgtgggcg ccgtccggac  10260
cggtacgccc cggcttggcc cgtgacgggt cgcacccgc cggggccac ggcgcgcgcc  10320
     SmaI
cccagccccc gggcccagca ccccaaggcg gccccggtg ccgcgcgcgg gggtcggggg  10380
cccgggtcgt ggggttccgc gccaacgcca aaactctccc tcctcctctt cctcaatctc  10440
gctctcgctc cggttgcggt tttgagaggg aggaggagaa ggagttagag cgagagcgag  10500
ttttttttt tcgcaaaagg aggggagagg gggtaaaaaa atgctgcact aaaaaaaaaa  10560
agcgttttcc tcccctctcc cccatttttt tacgacgtga gtgcggcgaa gccggtgagt  10620
gagcggcgcg gggccaatca gcgtgcgccg cacgccgctt cggccactca ctgccgcgc   10680
                                                         XhoI
cccggttagt cgcacgcggc ttccgaaagt tgcctttat ggctcgagcg gccgcggcgg  10740
cgccctataa aaggctttca acggaaaata ccgagctcgc cggcgccgcc gcgggatatt  10800
```

FIG. 7-6

```
aacccagcgg cgcgacgcgc caccaccgcc gagaccgcgt ccgcccgcga ttgggtcgcc  10860
gcgctgcgcg gtggtggcgg ctctggcgca ggcgggcgct gcacagagcc tcgcctttgc  10920
cgatccgccg cccgtccaca cccgccgcca cgtgtctcgg agcggaaacg gctaggcggc  10980
gggcaggtgt gggcggcggt ggtaagcccg gccagccgac cggggcatgc ggccgcggcc  11040
cttcgcccgt ccattcgggc cggtcggctg gcccgtacg ccggcgccgg gaagcgggca  11100
gcagagccgc cgtctgggcc gcagcggggg gcgcatgggg cggaaccgga cgtctcggcg  11160
gcagacccgg cgtcgccccc cgcgtacccc gccttggcct ccgccgtggg gggcgcggga  11220
gaagcccctg ggcctccgga gatgggggac ggcggcaccc cccgcgccct cttcggggac  11280
ccggaggcct ctacccctg acccacgcc agttcgcagg cgcgaggccg cgctcgggcg  11340
ggcgcgctcc tgggtgcgg tcaagcgtcc gcgctccggc gcgagccgc ccgcgcgagg  11400
gggggtgccg ctctcggggc gggggcaacc ggcggggtct ttgtctgagc ccccacggc  11460
gagagccccg ccccgttgg ccgcccaga aacagactcg cgggctcttg ccaatgggga  11520
tcgcacggtg ggcgcggcgt agccccgtc gcccgagaac ggttacccct agcgtgccac  11580
ccgcgccgca tcggggcag aggcccggtg ggggctgggg cgccatgcgc gtgcgcgctg  11640
gtcctttggg tccgggccac cccgacccc gcggtacgcg cacgcgcgac caggaaaccc  11700
cgctaactgc gtgcgcgctg ggaattggcg ctaattgcgc gtgcgcgctg gcgattgacg  11760
cacgcgcgac ccttaaccgc gattaacgcg cacgcgcgac ggactcaatg gcgctaatcg  11820
                        SmaI
cgcgtgcgtt ctggggcccg ggcgcttgcg cctgagttac cgcgattagc gcgcacgcaa  11880
gaccccgggc ccgcgaacgc ccacttcctg ccgagccgc tggcgcccga gggtgtggcc  11940
gctgcgtgcg ggtgaaggac gggctcggcg accgcgggct cccacaccgg cgacgcacgc  12000
cgcgcgcgac ccggtcgctg tttgaaccgg gcggaggcgg ggctggcgcc gcgcgcgctg  12060
ggccagcgac aaacttggcc cgcctccgcc ccgaccgcgg cggttgggag ggggttgggg  12120
cctggcttcc tgccgcgcgc cgcggggacg gccaacccct cccpaacccc ggaccgaagg  12180
acggcgcgcg gcgcccctgc cctccgacca gtgtttgcct tttatggtaa taacgcggcc  12240
ggcccggctt ggaggctggt cacaaacgga aataccatt attgccgg ccgggccgaa  12300
cctttgtccc caatctgggc gcgcgccggc gccccctggc ggcctaagga ggaaacaggg  12360
gttagacccg cgcgcggccg cgggggaccg ccggattcct ctcggcgcgc cggaagtggc  12420
cagggcgggg gcgacttcgg ctcacagcgc gagccgcgcg gccttcaccg gtccgcccc  12480
cgctgaagcc gagtgtcgcg gccggctat tctcgcagct caccatgccg gtcgccacca  12540
tgataccgtc cgggccgata agagcgtcga gtggtacggc cagcggtggt actatggcag  12600
gacctg                                                              12606
```

FIG. 7-7

SEQUENCE LISTING

<160> NUMBER OF SEQ ID NOS: 12

<210> SEQ ID NO 1
<211> LENGTH: 10464
<212> TYPE: DNA
<213> ORGANISM: Artificial Sequence
<220> FEATURE:
<223> OTHER INFORMATION: PDCD2/ACTIN ARTIFICIAL UCOE SEQUENCE

<400> SEQUENCE: 1

```
catggcacct gtattgtact cttatcagtc attatatgga ctttaacttc gtaccgtgga      60
cataacatga gaatagtcag taatatacct gaaattgaag cccagatatt atttgggctc     120
ctccataaga ctgtgagcat ctgaccactg gggtctataa taaacccgag gaggtattct     180
gacactcgta gactggtgac gagtgttgct tcccattata tccctgttat caagcacaag     240
gtcaggcaca ctcacaacga agggtaatat agggacaata gttcgtgttc cagtccgtgt     300
gagtaagact caaaacatgt tttggaatgt atgactggta tgaactacaa ctcattctga     360
gttttgtaca aaaccttaca tactgaccat acttgatgtt accagtaagc tgatgttttc     420
attttgagtc tataaatcta attttgtggt tggtcattcg actacaaaag taaaactcag     480
atatttagat taaaacacca ggttttgtgt atggctcaag gctcaaattg taaaatttaa     540
tattatgtga ccaaaacaca taccgagttc cgagtttaac attttaaatt ataatacact     600
ccaaagaaag ttatacccag aacctcaatt tcctcacctt caaaatgggg ggtttctttc     660
aatatgggtc ttggagttaa aggagtggaa gttttacccc cagtttctca ctcattggtc     720
tgctgtcacg attttaatga gctcatgcac gtcaaagagt gagtaaccag acgacagtgc     780
taaaattact cgagtacgtg aaacagccct ttatataagg taagtgctgg ataaatgttg     840
gctactataa tttgtcggga aatatattcc attcacgacc tatttacaac cgatgatatt     900
taaaataagc ctctaagata cttggtcagc acaagtacta cccaagagta attttattcg     960
gagattctat gaaccagtcg tgttcatgat gggttctcat tgcactgtaa gtaaactgac    1020
aaaattgtgt atctaaaact ggccagatga acgtgacatt catttgactg ttttaacaca    1080
tagattttga ccggtctact aagagaaact tttaaggggc ccttctgcgt gcccgacact    1140
gtgctaggca ttctctttga aaattcccccg ggaagacgca cgggctgtga cacgatccgt    1200
ctcacactat cccgacccga gaaaccgatc tgcgacccag aggaacttac gagtgtgata    1260
```

```
gggctgggct ctttggctag acgctgggtc tccttgaatg caagcctcca gcatcttgtg   1320
cagccctact catgggacca tctggatacc gttcggaggt cgtagaacac gtcgggatga   1380
gtaccctggt agacctatgg caccttgtc tttacaggga gcagaacaca cctcttatgt    1440
gtcagaaaac gtgggaacag aaatgtccct cgtcttgtgt ggagaataca cagtcttttg   1500
aaagtccagg aagtatattt ttacctgagg caatatctga aaattgtatg tttcaggtcc   1560
ttcatataaa aatggactcc gttatagact tttaacatac ctacagcctc caaagtgagt   1620
cttcctctca gtacctctct tctaggcaca gatgtcggag gtttcactca gaaggagagt   1680
catggagaga agatccgtgt tggagccctt tcttccaagt attatgttta accacttaat   1740
gaatgaagtc acctcgggaa agaaggttca taatacaaat tggtgaatta cttacttcag   1800
ctgaaactgc ttacccatgc tccctataat ctctgagtaa tcttcctttt gactttgacg   1860
aatgggtacg agggatatta gagactcatt agaaggaaaa ccacaacctc aggcataatc   1920
tcatcttctg tttctattac aatttcaaat ggtgttggag tccgtattag agtagaagac   1980
aaagataatg ttaaagttta tctggaaaaa ggaagttgtg gtctggaatt atatggtcca   2040
gatgatctga agaccttttt ccttcaacac cagacccttaa tataccaggt ctactagact  2100
aacaaaaagg acagcactat tagtaatcat ttagttttga agacagtcta ttgtttttcc   2160
tgtcgtgata atcattagta aatcaaaact tctgtcagat ataatttgct gtctctaaag   2220
tactatattc cctatagttc tggcatttta tattaaacga cagagatttc atgatataag   2280
ggatatcaag accgtaaaat gataaagggt cataaattaa atgcctatat ggtgacatta   2340
ttcagtgatt ctattcccca gtatttaatt tacggatata ccactgtaat aagtcactaa   2400
cagacttcac agcctttttt tttttttttac aaaggtgttc caggcatgaa gtctgaagtg  2460
tcggaaaaaa aaaaaaaatg tttccacaag gtccgtactt aaatttttaaa gtactatacc  2520
tttcctaatt ttacctttaa agttgtcctg tttaaaattt catgatatgg aaaggattaa   2580
aatggaaatt tcaacaggac gaaatatctg ggttgacaaa ggcgatgaaa ctgaactgag   2640
acttaaaaaa ctttatagac ccaactgttt ccgctacttt gacttgactc tgaattttt    2700
aagattaccc acctggttgt gcacaagcct gcttatgtcc caatctccag ttctaatggg   2760
tggaccaaca cgtgttcgga cgaatacagg gttagaggtc tctagggtct gatgctcctt   2820
gctgcagtaa tatgctttgt ggcatctgga agatcccaga ctacgaggaa cgacgtcatt   2880
atacgaaaca ccgtagacct gcacgttttg gggcctaaac agccacaaac cctgcagaga   2940
tgagcaccag cgtgcaaaac cccggatttg tcggtgtttg ggacgtctct actcgtggtc   3000
acttaagctg gagacacact gattctcctg tttctggggg aggattctca tgaattcgac   3060
ctctgtgtga ctaagaggac aaagaccccc tcctaagagt gaaggtggct catatgagta   3120
aaaatcgttt ttcctgggta gttgattcct cttccaccga gtatactcat ttttagcaaa   3180
aaggacccat caactaagga aaaactaaa aaagaataca gagaaaagtt ttatcttcaa    3240
acaaaacagc tttttgattt tttcttatgt ctcttttcaa aatagaagtt tgttttgtcg   3300
aattcacata ttttatcctc tgcacgtaaa actgaaaata caacaacaa ttaagtgtat    3360
aaaataggag acgtgcattt tgactttat tgttgttgtt aaaagaaatg aaagttttg     3420
ctttcaggaa taagcttta aaatccagaa ttttctttac tttcaaaaac gaaagtcctt   3480
attcgaaaat tttaggtctt actagatttc gtccggtaca cgcaactgag ttgcctccta   3540
gaggtggttt tgatctaaag caggccatgt gcgttgactaa aacggaggat ctccaccaaa  3600
```

```
gagttaatca aattaataag actgatcgtt aagaacgact gccaaaaata ctcaattagt    3660
ttaattattc tgactagcaa ttcttgctga cggtttttat cgaaaaagct actgggatcc    3720
atctttccaa gacaatttct attatctgaa gcttttcga tgaccctagg tagaaaggtt    3780
ctgttaaaga taatagactt ttaacaccat acctggtacc cactgattaa aagctggggg    3840
ttaccaatgc aattgtggta tggaccatgg gtgactaatt ttcgaccccc aatggttacg    3900
gcgtgggcac agttagaagc ttatgtagca aaaatgagca catcctggaa cgcacccgtg    3960
tcaatcttcg aatacatcgt ttttactcgt gtaggacctt gggcccggga gaaggtgctc    4020
ctggggcagc gcggagaggg agctctgagg cccgggccct cttccacgag gaccccgtcg    4080
cgcctctccc tcgagactcc ctggggcggc agcggtgctt ccgccgtcc cctggtcgc    4140
tcccggaatt gaccccgccg tcgccacgaa cggcggcagg gggaccagcg agggccttaa    4200
aacgccgcgc acgcgtcgga ggcatggccc cgtcccgacc ccgtttggcg ttgcggcgcg    4260
tgcgcagcct ccgtaccggg gcagggctgg gcaaaccgc gctcacctcg caggccggca    4320
cagcacggct gctcgcggca gcagaagagg cgagtggagc gtccggccgt gtcgtgccga    4380
cgagcgccgt cgtcttctcc aagatgcagc ggtggaaggc gtccggcgg ccaggcagcg    4440
gcgcatacac ttctacgtcg ccaccttccg caggcccgcc ggtccgtcgc cgcgtatgtg    4500
ctgcagcaga aggagagcg ggcggccgca cagctcgcag gccagggcct gacgtcgtcc    4560
ttcctctcgc ccgccggcgt gtcgagcgtc cggtcccgga ggggcccgg cagcccggcc    4620
gcgcccagcc atgccggccg cccgcccacc ccccggggcc gtcgggccgg cgcgggtcgg    4680
tacggccggc gggcgggtgg ttgctgggga actgctcgct gcgcagtcgc cacgccggcg    4740
ccgactcgga aacgacccct tgacgagcga cgcgtcagcg gtgcggccgc ggctgagccg    4800
gaagcccagc tccacaggcc tggccccggc ggcagccatg cggggcgcgg cttcgggtcg    4860
aggtgtccgg accggggccg ccgtcggtac gccccgcgcc gctggcgtgg ggcgcagccc    4920
acagctgggt cggaaggcgg aaatcgggcg cgaccgcacc ccgcgtcggg tgtcgaccca    4980
gccttccgcc tttagcccgc ccgggccgga aggcaagagg cgggcacctt tccggaggac    5040
aggaggcgga ggcccggcct tccgttctcc gcccgtggaa aggcctcctg tcctccgcct    5100
aacgcgtctg acgggagcgg ttgcaggacc aatgcgaggg aacggggcag ttgcgcagac    5160
tgccctcgcc aacgtcctgg ttacgctccc ttgccccgtc aggaaacctc tcggcatcag    5220
ccccgcccct ggcgcctctg cctccgagcc tcctttggag agccgtagtc ggggcgggga    5280
ccgcggagac ggaggctcgg gctttcctgg tgcctccggg tgctctggga tggttctggt    5340
ctttgggaga cgaaaggacc acggaggccc acgagaccct accaagacca gaaaccctct    5400
gtggcagctg gtgacggcgc tccgctcacc tctgcacatg tcttgctgtg caccgtcgac    5460
cactgccgcg aggcgagtgg agacgtgtac agaacgacac ggcctgcggg tggccgccag    5520
ggaggcagag ccctcccgca aaccttccct ccggacgccc accggcggtc cctccgtctc    5580
gggagggcgt ttggaaggga gctggtgtcc acctcagggt gtgggaaacc tgtgcgctgg    5640
ccgagtgcta cgaccacagg tggagtccca caccctttgg acacgcgacc ggctcacgat    5700
accaagagta ggcagtgaaa gacaaatgaa ggttgaacag gtaaagtgag tggttctcat    5760
ccgtcacttt ctgtttactt ccaacttgtc catttcactc gacccctacag cggaaaccaa    5820
gaatcctgtg tgcctgagag taatgaagaa ctgggatgtc gcctttggtt cttaggacac    5880
acggactctc attacttctt gcctctgcag aagagtcttt tctgtcagtc ttaaggtctc    5940
tgttttaatg cggagacgtc ttctcagaaa agacagtcag aattccagag acaaaattac    6000
```

```
ttagtgctgg cttgctgtac ctgaattcca agggaggagt gtataatgag aatcacgacc   6060
gaacgacatg gacttaaggt tccctcctca catattactc gcatggccaa cccccacttc   6120
ccatcattgc ctgaactagt ttttcaggtt cgtaccggtt gggggtgaag ggtagtaacg   6180
gacttgatca aaaagtccaa aacttcagaa tgcccttggt accgcgggcc ccctctgtgg   6240
tcccacgcca ttgaagtctt acgggaacca tggcgcccgg gggagacacc agggtgcggt   6300
ctgatcgctg catgcccacc acctgggtac acacagtctg tgattcccgg gactagcgac   6360
gtacgggtgg tggacccatg tgtgtcagac actaagggcc agcagaacgg accctgccca   6420
cccggtcttg tgtgctactc agtggacaga tcgtcttgcc tgggacgggt gggccagaac   6480
acacgatgag tcacctgtct cccaaggcaa gaaagggtga caaggacagg gtcttcccag   6540
gctggctttg gggttccgtt ctttcccact gttcctgtcc cagaagggtc cgaccgaaac   6600
agttcctagc accgcccgc ccccaatcct ctgtggcaca tggagtcttg tcaaggatcg   6660
tggcggggcg ggggttagga gacaccgtgt acctcagaac gtccccagag tcccccagcg   6720
gcctccagat ggtctgggag ggcagttcag caggggtctc aggggtcgc ggaggtcta   6780 ccagaccctc ccgtcaagtc ctgtggctgc gcatagcaga catacaacgg acggtgggcc   6840
cagacccagg gacaccgacg cgtatcgtct gtatgttgcc tgccaccgg gtctgggtcc   6900 ctgtgtagac ccagccccc cgcccgcag tgcctaggtc acccactaac gacacatctg   6960
ggtcgggggg gcgggcgtc acggatccag tgggtgattg gccccaggcc tggtcttggc   7020
tgggcgtgac tgttaccctc aaaagcaggc cggggtccgg accagaaccg accgcactg   7080 acaatgggag ttttcgtccg agctccaggg taaaaggtgc cctgccctgt agagcccact   7140
tccttcccag tcgaggtccc attttccacg ggacgggaca tctcgggtga aggaagggtc   7200
ggctgcggct gggtaggttt gtagccttca tcacgggcca cctccagcca ccgacgccga   7260
cccatccaaa catcggaagt agtgcccggt ggaggtcgt ctggaccgct ggcccctgcc   7320
ctgtcctggg gagtgtggtc ctgcgactct gacctggcga ccggggacgg gacaggaccc   7380
ctcacaccag gacgctgaga aatggccgca agccacctga ctcccccaac accacactct   7440
acctctcaag ttaccggcgt tcggtggact gagggggttg tggtgtgaga tggagagttc   7500
cccaggtctc tccctagtga cccacccagc acatttagct agctgagccc gggtccagag   7560
agggatcact gggtgggtcg tgtaaatcga tcgactcggg cacagccaga ggtcctcagg   7620
ccctgctttc agggcagttg ctctgaagtc gtgtcggtct ccaggagtcc gggacgaaag   7680
tcccgtcaac gagacttcag ggcaaggggg agtgactgcc tggccactcc atgccctcca   7740
agagctcctt ccgttccccc tcactgacgg accggtgagg tacgggaggt tctcgaggaa   7800
ctgcaggagc gtacagaacc cagggccctg gcacccgtgc agaccctggc gacgtcctcg   7860
catgtcttgg gtcccgggac cgtgggcacg tctgggaccg ccaccccacc tgggcgctca   7920
gtgcccaaga gatgtccaca cctaggatgt ggtgggtgg accgcgagt cacgggttct   7980 ctacaggtgt ggatcctaca cccgcggtgg gtgggggcc cgagagacgg gcaggccggg   8040
ggcaggcctg ggcgccacc accccccgg gctctctgcc cgtccggccc ccgtccggac   8100
gccatgcggg gccgaaccgg gcactgccca gcgtggggcg cggggccac cggtacgccc   8160 cggcttggcc cgtgacgggt cgcacccgc gccccggtg ggcgcgcgcc cccagccccc   8220
gggcccagca ccccaaggcg gccaacgcca ccgcgcgcgg gggtcggggg cccgggtcgt   8280
ggggttccgc cggttgcggt aaactctccc tcctcctctt cctcaatctc gctctcgctc   8340
```

-continued

```
tttttttttt tttgagaggg aggaggagaa ggagttagag cgagagcgag aaaaaaaaaa    8400
tcgcaaaagg agggggagagg gggtaaaaaa atgctgcact gtgcggcgaa agcgttttcc    8460
tccCctctcc cccatttttt tacgacgtga cacgccgctt gccggtgagt gagcggcgcg    8520
gggccaatca gcgtgcgccg ttccgaaagt cggccactca ctcgccgcgc cccggttagt    8580
cgcacgcggc aaggctttca tgcctttat ggctcgagcg gccgcggcgg cgccctataa    8640
aacccagcgg acggaaaata ccgagctcgc cggcgccgcc gcgggatatt ttgggtcgcc    8700
cgcgacgcgc caccaccgcc gagaccgcgt ccgcccgcga gcacagagcc gcgctgcgcg    8760
gtggtggcgg ctctggcgca ggcgggcgct cgtgtctcgg tcgcctttgc cgatccgccg    8820
cccgtccaca cccgccgcca ggtaagcccg agcggaaacg gctaggcggc gggcaggtgt    8880
gggcggcggt ccattcgggc gccagccgac cggggcatgc ggccgcgcc cttcgcccgt    8940 gcagagccgc cggtcggctg gccccgtacg ccggcgccgg gaagcgggca cgtctcggcg    9000
cgtctgggcc gcagcggggg gcgcatgggg cggaaccgga ccgccgtggg gcagacccgg    9060
cgtcgccccc cgcgtacccc gccttggcct ggcggcaccc gggcgcggga aagcccctg    9120 ggcctccgga gatgggggac accccacgcc ccgcgccct cttcggggac ccggaggcct    9180
ctaccccctg tggggtgcgg agttcgcagg cgcgaggccg cgctcgggcg ggcgcgctcc    9240
gggggtgccg tcaagcgtcc gcgctccggc gcgagcccgc ccgcgcgagg ccccacggc    9300 ctctcggggc gggggcaacc ggcggggtct ttgtctgagc cgggctcttg gagagccccg    9360
cccccgttgg ccgccccaga aacagactcg gcccgagaac ccaatgggga tcgcacggtg    9420
ggcgcggcgt agccccgtc aggcccggtg ggttacccct agcgtgccac ccgcgccgca    9480 tcggggcag tccgggccac ggggctgggg cgccatgcgc gtgcgcgctg gtcctttggg    9540
cgctaactgc ccccgacccc gcggtacgcg cacgcgcgac caggaaaccc gcgattgacg    9600
gtgcgcgctg ggaattggcg ctaattgcgc gtgcgcgctg ggactcaatg cacgcgcgac    9660
ccttaaccgc gattaacgcg cacgcgcgac cctgagttac gcgctaatcg cgcgtgcgtt    9720
ctggggcccg ggcgcttgcg ccacttcctg cgcgattagc gcgcacgcaa gaccccgggc    9780
ccgcgaacgc ggtgaaggac cccgagccgc tggcgcccga gggtgtggcc gctgcgtgcg    9840
cgcgcgcgac gggctcggcg accgcgggct cccacaccgg cgacgcacgc gcgcgcgctg    9900
ccggtcgctg tttgaaccgg gcggaggcgg ggctggcgcc cggttgggag ggccagcgac    9960
aaacttggcc cgcctccgcc ccgaccgcgg gccaaccctc ggggttgggg cctggcttcc   10020
tgccgcgcgc cgcggggacg cctccgacca ccccaacccc ggaccgaagg acggcgcgcg   10080
gcgcccctgc ggaggctggt gtgtttgcct tttatggtaa taacgcggcc ggcccggctt   10140
cctttgtccc cacaaacgga aaataccatt attgcgccgg ccgggccgaa ggaaacaggg   10200
caatctgggc gcgcgccggc gcccctggc ggcctaagga ctcggcgcgc gttagacccg   10260
cgcgcggccg cggggaccg ccggattcct gagccgcgcg cggaagtggc cagggcgggg   10320
gcgacttcgg ctcacagcgc gcccggctat gccttcaccg gtcccgcccc cgctgaagcc   10380
gagtgtcgcg cgggccgata tctcgcagct caccatgccg gtcgccacca tgagagcgtc   10440
gagtggtacg gccagcggtg gtac                                          10464
```

<210> SEQ ID NO 2
<211> LENGTH: 12606
<212> TYPE: DNA
<213> ORGANISM: Artificial Sequence
<220> FEATURE:
<223> OTHER INFORMATION: RNP/HP-1/ACTIN ARTIFICIAL UCOE SEQUENCE

<400> SEQUENCE: 2

```
aagcttactt gattggccat gtggcaagcg acaggcacaa acaattttc ttcgaatgaa      60
ctaaccggta caccgttcgc tgtccgtgtt ttgttaaaag caagtcaata ggaaaaacct    120
cagagctgaa atctttatat gctgtactac gttcagttat ccttttttgga gtctcgactt   180
tagaaatata cgacatgatg acagctgtat tctgggcact tatgaatgtt aaggaaacct    240
gtcttaaaag tgtcgacata agacccgtga atacttacaa ttcctttgga cagaattttc    300
ttaactaggt taaaaaacct caaacgagag aaagtgatat ccaggaccaa aattgatcca    360
attttttgga gtttgctctc tttcactata ggtcctggtt ctgctacaaa cgcataatgc    420
aaactaaaaa gtcacacgta attttcaatc gacgatgttt gcgtattacg tttgattttt    480
cagtgtgcat taaaagttag aattatttt tgttcctagc aagcagcatt aattgctgct    540
ctcatcccag ttaataaaaa acaaggatcg ttcgtcgtaa ttaacgacga gagtagggtc    600
ttctacggag ctctccctcc attcgcatgc tcccaactcc taaaaagtag aagatgcctc    660
gagagggagg taagcgtacg agggttgagg attttttcatc tggtaaaacc cagttcagat   720
ttttttttcct gtagttttca tgactcgtaa accatttttgg gtcaagtcta aaaaaaagga   780
catcaaaagt actgagcatt aaattaaaga aaaaattaac tgaaatgatc aaactagctc    840
ctatgagaca tttaatttct ttttaattg actttactag tttgatcgag atactctgt     900
caaagcagtc ttttgaaatg gttacttgtc acgatagtta ttttcattt gtttcgtcag    960
aaaactttac caatgaacag tgctatcaat aaaagtaaaa ttcagctagt ttttattctt  1020
aattgtcgtc agcacatagg ttatctctaa aagtcgatca aaaataagaa ttaacagcag  1080
tcgtgtatcc aatagagatt actgaaatta cggataatgt acatttataa caagttttac  1140
aaatcactaa tgactttaat gcctattaca tgtaaatatt gttcaaaatg tttagtgatt  1200
caaaaagcaa aaactcatta cttacctcac aatttatcca aacttacccg ttttttcgtt  1260
tttgagtaat gaatggagtg ttaaataggt ttgaatgggc atgtccacta tcgattttaa  1320
acaatgttat tttataaacg tgcttagggt tacaggtgat agctaaaatt tgttacaata  1380
aaatatttgc acgaatccca caaagaaaaa taaccaggta gacccccttc gcttgagacc  1440
ttatgcttat gtttctttttt attggtccat ctgggggaag cgaactctgg aatacgaata  1500
caatgtaatg ttcaaccaag attgcaaaca aaatgagaaa agtaacaaag gttacattac  1560
aagttggttc taacgtttgt tttactcttt tcattgtttc ttcaaataca gagcggccca  1620
ggcccaaaac agttttgcac atcaatccat aagtttatgt ctcgccgggt ccgggttttg  1680
tcaaaacgtg tagttaggta acgcattaca ggaaggagcc tctgaagcca tgttttaatc  1740
gaagtataac tgcgtaatgt ccttcctcgg agacttcggt acaaaattag cttcatattg  1800
taaggacaaa atcgttattt cactttcctc gtaatcatct ataaaggtcc attcctgttt  1860
tagcaataaa gtgaaaggag cattagtaga tatttccagg atggatctgt cccgtaaggg  1920
ttaaacttct cagtaacaac attacttaaa tacctagaca gggcattccc aatttgaaga  1980
gtcattgttg taatgaattt atgagtcagc tctacaactt aaacggaatc cttaagaaca  2040
gtaaaggatt tactcagtcg agatgttgaa tttgccttag gaattcttgt catttcctaa  2100
ctgacgcgaa tatccctccc ccgcccagaa aaccaccttc gtccctgccc gactgcgctt  2160
atagggaggg ggcgggtctt ttggtggaag cagggacggg ctcgtggccg atggcttcca  2220
atttatgttt attttgccgc ggttcatctg gagcaccggc taccgaaggt taaatacaaa  2280
```

```
taaaacggcg ccaagtagac tcgttttact gactgcagac ccagataaaa ccgttactca    2340
aaggaaaaaa agcaaaatga ctgacgtctg ggtctatttt ggcaatgagt ttccttttt     2400 aagacaggaa aaacataaaa tggtttcttt gtcctacggc tcgcattgaa ttctgtcctt    2460
tttgtatttt accaaagaaa caggatgccg agcgtaactt cccggcccga cgccctgggt    2520
ggtgatatct tctctgaaac cgggcccgca gggccgggct gcgggaccca ccactataga    2580
agagactttg gcccgggcgt aacccggagc acccccctc cccgctcttc ggtgtggctt     2640
ccgaacgcaa ttgggcctcg tgggggggag gggcgagaag ccacaccgaa ggcttgcgtt    2700
tggcgccatt tcatcgaggg gaaggctgag cgcctttaat gaggtgcgca accgcggtaa    2760
agtagctccc cttccgactc gcggaaatta ctccacgcgt ggactctaaa gatccaagct    2820
cacaaaacac tccaaatcca cctcgaaacg cctgagattt ctaggttcga gtgttttgtg    2880
aggtttaggt ggagctttgc atatgaaaac agcccgagaa gaaaaaaaaa atagttaacc    2940
acttctactt tatactttg tcgggctctt ctttttttt tatcaattgg tgaagatgaa      3000
cttgatagag aaagcacact aagaaaataa agagttata aggaaaacgc gaactatctc     3060
tttcgtgtga ttcttttatt ttctcaatat tccttttgcg tgagaggaag gcgagccatg    3120
aaaatggcgg ccgccaaatc ggttcccggg actctccttc cgctcggtac ttttaccgcc    3180
ggcggtttag ccaagggccc agagaggggg aggggaagct ccgcagcctc gctcacgagg    3240
acctgctgcc tctctccccc tcccttcga ggcgtcggag cgagtgctcc tggacgacgg     3300
cgccgaaacg ctcgccgagg agacgccgtg gcccccgaag cagcgtgctt gcggctttgc    3360
gagcggctcc tctgcggcac cggggcttc gtcgcacgaa tagaaaggga ataagaattc     3420
ccgcctccgc gccccacttt caccccagcg atctttccct tattcttaag ggcggaggcg    3480
cggggtgaaa gtggggtcgc gggcagcgtc cgccatgtga aagctcccca tcccccaccc   3540
ccagtgaagg cccgtcgcag gcggtacact ttcgaggggt aggggtggg ggtcacttcc     3600 gaaatggcgc cgggaggctg agggtgggga agctgtttgt acgctcaggc ctttaccgcg    3660
gccctccgac tcccaccccct tcgacaaaca tgcgagtccg ctccgctcaa gaccccgttc   3720 ataaaccta agccccactg ctactgaatt gaggcgagtt ctggggcaag tatttggaat     3780
tcggggtgac gatgacttaa ggtccgattt cctgcctctc tcccacggag gcggctggcc    3840
gacttccact ccaggctaaa ggacggagag agggtgcctc cgccgaccgg ctgaaggtga    3900
gaggcgccaa cggcctcgcc atgcccttt caataactca ttgatttcaa ctccgcggtt     3960
gccggagcgg tacgggaaaa gttattgagt aactaaagtt acccgttacc tccatcgcgg    4020
actcagtcgc ttcagcccga ttttcccgcag tgggcaatgg aggtagcgcc tgagtcagcg   4080
aagtcgggct aaagggcgtc ccgagcgaga tgagagagat ctccgcggac gaacacgaac    4140
cggactcgtc ggctcgctct actctctcta gaggcgcctg cttgtgcttg gcctgagcag    4200
ctggcgctgt agtgagaact gccgctgctc gagaaacaac tctgcgagga gaccgcgaca    4260
tcactcttga cggcgacgag ctctttgttg agacgctcct gcacctccgc acgggacccg    4320
gcgctgctgc tactgccgct agagccgctg cgtggaggcg tgccctgggc cgcgacgacg    4380
atgacggcga tctcggcgac ccgccgcttt tctagaacct tcccccccac taacgcgtct    4440
tccgctacgt ggcggcgaaa agatcttgga agggggggtg attgcgcaga aggcgatgca   4500
caggccgtcg cgtaaacgcc ctatccgccg ccaatggcgg gaaggctcta gtccggcagc    4560
gcatttgcgg gataggcggc ggttaccgcc cttccgagat cgcccacct tacgccaaat     4620 gcgtactcct cccaccctg cggccagaga gcggggtgga atgcggttta cgcatgagga     4680
```

-continued

| | |
|---|---|
| gggtgggaac gccggtctct cagtacccga cgttacttcc gtaaatgcgc tcaatgaatt | 4740 |
| gcggaaggct gtcatgggct gcaatgaagg catttacgcg agttacttaa cgccttccga | 4800 |
| agagtcctgc tagttactac ctcttggaat agggtcccgg cccctgcctt tctcaggacg | 4860 |
| atcaatgatg gagaacctta tcccagggcc ggggacggaa ggcgaaggca ggtgagaaac | 4920 |
| gtcgcgcagt ttgaaattaa cgccgacggg ccgcttccgt ccactctttg cagcgcgtca | 4980 |
| aactttaatt gcggctgccc aggggcttaa tccgcagcct ggagatccag cccctcaac | 5040 |
| ccggaggtg tccccgaatt aggcgtcgga cctctaggtc gggggagttg ggccctccac | 5100 |
| gtccctgcag ttacgccaat gataacccc gccagaaaaa tcttagtagc cagggacgtc | 5160 |
| aatgcggtta ctattggggg cggtcttttt agaatcatcg cttccctttt tgttttccgt | 5220 |
| gccccaactc ggcggattga ctcggcccct gaagggaaaa acaaaaggca cggggttgag | 5280 |
| ccgcctaact gagccgggga tccggaaaca cccgaatcaa cttctagtca aattattgtt | 5340 |
| cacgccgcaa aggcctttgt gggcttagtt gaagatcagt ttaataacaa gtgcggcgtt | 5400 |
| tgacccaccc ctggcccgcg tctgtggaac tgacccctgg tgtacaggag actgggtggg | 5460 |
| gaccgggcgc agacaccttg actggggacc acatgtcctc agttcgctgc tgaaagtggt | 5520 |
| cccaaagggg tactagtttt taagctccca tcaagcgacg actttcacca gggtttcccc | 5580 |
| atgatcaaaa attcgagggt actccccctc ccccagcgtc tggaggattc cacaccctcg | 5640 |
| caccggcggg tgaggggag ggggtcgcag acctcctaag gtgtgggagc gtggccgccc | 5700 |
| cgaggaagtg ggcggagtcc ggttttggcg ccagccgctg aggctgccaa gctccttcac | 5760 |
| ccgcctcagg ccaaaaccgc ggtcggcgac tccgacggtt gcagaaaagc caccgctgag | 5820 |
| gagactccgg tcactgtcct cgccccgcct cgtcttttcg gtggcgactc ctctgaggcc | 5880 |
| agtgacagga gcggggcgga ccccctttccc tcccccttggg gaccaccggg cgccacgccg | 5940 |
| cgaacggtaa gggggaaggg aggggaaccc ctggtggccc gcggtgcggc gcttgccatt | 6000 |
| gtgccgcggt cgtcggcgcc tccgccctcc ccctagggcc ccaattccca cacggcgcca | 6060 |
| gcagccgcgg aggcgggagg gggatcccgg ggttaagggt gcgggcgcgg cgccggcccc | 6120 |
| tccccccgcc gcgcgcgcgc ccgctgcccc cgcccgcgcc gcggccgggg agggggggcgg | 6180 |
| cgcgcgcgcg ggcgacgggg gcccttcgtg gccgcccggc gtgggcggtg ccacccctcc | 6240 |
| ccccggcggc cgggaagcac cggcgggccg cacccgccac ggtggggagg ggggccgccg | 6300 |
| cccgcgcgca gctcccggct ccctccccct tcggatgtgg cttgagctgt gggcgcgcgt | 6360 |
| cgagggccga gggaggggga agcctacacc gaactcgaca aggcgcggag ggccggagac | 6420 |
| gctgcagacc cgccgacccgg agcagctcgg tccgcgcctc ccggcctctg cgacgtctgg | 6480 |
| gcgctgggcc tcgtcgagcc aggcggtgaa gtcggtggct ttccttctct ctagctctcg | 6540 |
| ctcgctggtg tccgccactt cagccaccga aaggaagaga gatcgagagc gagcgaccac | 6600 |
| gtgcttcaga tgccacacgc gtcccggggg cccggttctc cgctcccctc cacgaagtct | 6660 |
| acggtgtgcg cagggccccc gggccaagag gcgaggggag ccctccccttt ctcgccggac | 6720 |
| cccgcgccgg gagctgcggg aaggagtgga gggagggggaa gagcggcctg gggcgcggcc | 6780 |
| ctcgacgccc ttcctcacct gggtcgggcg gtggcctcgc ggctggcctg gcgcgcggcc | 6840 |
| agcccggtag cccagcccgc caccggagcg ccgaccggac cgcgcgccgg tcgggccatc | 6900 |
| ttagtggggg gactgctctg ccctcgaggg ggtagggagc tgtggcgacg aatcacccc | 6960 |
| ctgacgagac gggagctccc ccatccctcg acaccgctgc gttgccccat ttcgagacaa | 7020 |

-continued

| | |
|---|---|
| agcgcatttc cccctcccct ccccaccccg caacggggta aagctctgtt tcgcgtaaag | 7080 |
| ggggagggga gggggtgggc cgttccggcg gaggcgcccc ctcccccagc gccacgcggg | 7140 |
| gctgggtcga gcaaggccgc ctccgcgggg gaggggggtcg cggtgcgccc cgacccagct | 7200 |
| gacttgggcc tcccggaggg cggcgcgtgg tcccgcgtcc gcgagcctgg ctgaacccgg | 7260 |
| agggcctccc gccgcgcacc agggcgcagg cgctcggacc cggcgcgcgg ccggctgtcc | 7320 |
| cgaggctgcg gcgaccgcca gttaacgtgg gccgcgcgcc ggccgacagg gctccgacgc | 7380 |
| cgctggcggt caattgcacc ccgcgcgggg gtaggcgcgt gcggtgtggc gcagtgccct | 7440 |
| tgagcccccg ggcgcgcccc catccgcgca cgccacaccg cgtcacggga actcgggggc | 7500 |
| tgccgcggcc tttgtttctc cccgcggatg cgctgaccac gaggcccgcg acggcgccgg | 7560 |
| aaacaaagag gggcgcctac gcgactggtg ctccgggcgc ctcccgggtg ggggcgggca | 7620 |
| cccgcgctta ggcctctgga cgccgggctt gagggcccac cccgcccgt gggcgcgaat | 7680 |
| ccggagacct gcgccccgaa cagcggcggg ggtcgggagc gggtgtttgc aagaggtgat | 7740 |
| tctttttttca gtcgccgccc ccagccctcg cccacaaacg ttctccacta agaaaaagt | 7800 |
| aagtgtcacg aaacggggtt gaagcatctt aagttttttc cttttgttat ttcacagtgc | 7860 |
| tttgccccaa cttcgtagaa ttcaaaaaag gaaaacaata ttaattaccg attggaaaga | 7920 |
| gggagggttt ctgagcagaa accaagttgg aattaatggc taacctttct ccctcccaaa | 7980 |
| gactcgtctt tggttcaacc gattgcagaa cagagaagat tcacagtgct ttaccgttgt | 8040 |
| gagttgtttg ctaacgtctt gtctcttcta agtgtcacga aatggcaaca ctcaacaaac | 8100 |
| ggtaatcgtg cctggttttta aaccgaaagg attgtccttt aaaaatggaa ccattagcac | 8160 |
| ggaccaaaat ttggctttcc taacaggaaa ttttttacctt catggacttt attataaatg | 8220 |
| ggacttagat tggaaaagac attggtcccc gtacctgaaa taatatttac cctgaatcta | 8280 |
| acctttttctg taaccagggg tattttaagc catgtgaagc tgttttaggt accgcgggcc | 8340 |
| ccctctgtgg ataaaattcg gtacacttcg acaaaatcca tggcgcccgg gggagacacc | 8400 |
| tcccacgcca ctgatcgctg catgcccacc acctgggtac acacagtctg agggtgcggt | 8460 |
| gactagcgac gtacgggtgg tggacccatg tgtgtcagac tgattcccgg agcagaacgg | 8520 |
| accctgccca cccggtcttg tgtgctactc actaagggcc tcgtcttgcc tgggacgggt | 8580 |
| gggccagaac acacgatgag agtggacaga cccaaggcaa gaaagggtga caaggacagg | 8640 |
| gtcttcccag tcacctgtct gggttccgtt cttccccact gttcctgtcc cagaagggtc | 8700 |
| gctggctttg agttcctagc accgccccgc ccccaatcct ctgtggcaca cgaccgaaac | 8760 |
| tcaaggatcg tggcggggcg ggggttagga gacaccgtgt tggagtcttg gtccccagag | 8820 |
| tcccccagcg gcctccagat ggtctgggag acctcagaac caggggtctc aggggtcgc | 8880 |
| cggaggtcta ccagaccctc ggcagttcag ctgtggctgc gcatagcaga catacaacgg | 8940 |
| acggtgggcc ccgtcaagtc gacaccgacg cgtatcgtct gtatgttgcc tgccacccgg | 9000 |
| cagacccagg ctgtgtagac ccagccccc cgccccgcag tgcctaggtc gtctgggtcc | 9060 |
| gacacatctg ggtcgggggg gcgggggcgtc acggatccag acccactaac gccccaggcc | 9120 |
| tggtcttggc tgggcgtgac tgttacccct ctgggtgattg cggggtccgg accagaaccg | 9180 |
| acccgcactg acaatgggag aaaagcaggc agctccaggg taaaaggtgc cctgccctgt | 9240 |
| agagcccact ttttcgtccg tcgaggtccc attttccacg ggacgggaca tctcgggtga | 9300 |
| tccttcccag ggctgcggct gggtaggttt gtagccttca tcacgggcca aggaagggtc | 9360 |
| ccgacgccga cccatccaaa catcggaagt agtgcccggt cctccagcca ctggaccgct | 9420 |

```
ggcccctgcc ctgtcctggg gagtgtggtc ggaggtcggt gacctggcga ccggggacgg   9480
gacaggaccc ctcacaccag ctgcgactct aatggccgca agccacctga ctcccccaac   9540
accacactct gacgctgaga ttaccggcgt tcggtggact gaggggggttg tggtgtgaga   9600
acctctcaag cccaggtctc tccctagtga cccacccagc acatttagct tggagagttc   9660
gggtccagag agggatcact gggtgggtcg tgtaaatcga agctgagccc acagccaga    9720
ggtcctcagg ccctgctttc agggcagttg tcgactcggg gtgtcggtct ccaggagtcc   9780
gggacgaaag tcccgtcaac ctctgaagtc ggcaaggggg agtgactgcc tggccactcc   9840
atgccctcca gagacttcag ccgttccccc tcactgacgg accggtgagg tacgggaggt   9900
agagctcctt ctgcaggagc gtacagaacc cagggccctg gcacccgtgc tctcgaggaa   9960
gacgtcctcg catgtcttgg gtcccgggac cgtgggcacg agaccctggc ccaccccacc  10020
tgggcgctca gtgcccaaga gatgtccaca tctgggaccg gtgggggtgg acccgcgagt  10080
cacgggttct ctacaggtgt cctaggatgt cccgcggtgg gtgggggggcc cgagagacgg  10140
gcaggccggg ggatcctaca gggcgccacc cacccccccgg gctctctgcc cgtccggccc  10200
ggcaggcctg gccatgcggg gccgaaccgg gcactgccca gcgtggggcg ccgtccggac  10260
cggtacgccc cggcttggcc cgtgacgggt cgcaccccgc cggggggccac ggcgcgcgcc  10320
cccagccccc gggcccagca ccccaaggcg ccccccggtg ccgcgcgcgg gggtcggggg  10380
cccgggtcgt ggggttccgc gccaacgcca aaactctccc tcctcctctt cctcaatctc  10440
gctctcgctc cggttgcggt tttgagaggg aggaggagaa ggagttagag cgagagcgag  10500
tttttttttt tcgcaaaagg agggggagagg gggtaaaaaa atgctgcact aaaaaaaaaa  10560
agcgttttcc tccctctcc cccattttttt tacgacgtga gtgcggcgaa gccggtgagt  10620
gagcggcgcg gggccaatca gcgtgcgccg cacgccgctt cggccactca ctcgccgcgc  10680
cccgttagt cgcacgcggc ttccgaaagt tgccttttat ggctcgagcg gccgcggcgg  10740
cgccctataa aaggctttca acggaaaata ccgagctcgc cggcgccgcc gcgggatatt  10800
aacccagcgg cgcgacgcgc caccaccgcc gagaccgcgt ccgcccgcga ttgggtcgcc  10860
gcgctgcgcg gtggtggcgg ctctggcgca ggcgggcgct gcacagagcc tcgcctttgc  10920
cgatccgccg cccgtccaca cccgccgcca cgtgtctcgg agcggaaacg gctaggcggc  10980
gggcaggtgt gggcggcggt ggtaagcccg gccagccgac cggggcatgc ggccgcggcc  11040
cttcgcccgt ccattcgggc cggtcggctg gccccgtacg ccggcgccgg gaagcgggca  11100
gcagagccgc cgtctgggcc gcagcggggg gcgcatgggg cggaaccgga cgtctcggcg  11160
gcagaccccgc cgtcgccccc cgcgtacccc gccttggcct ccgccgtggg gggcgcggga  11220
gaagcccctg ggcctccgga gatgggggac ggcggcaccc cccgcgccct cttcggggac  11280
ccggaggcct ctacccccctg accccacgcc agttcgcagg cgcgaggccg cgctcgggcg  11340
ggcgcgctcc tggggtgcgg tcaagcgtcc gcgctccggc gcgagcccgc ccgcgcgagg  11400
gggggtgccg ctctcgggc gggggcaacc ggcgggtct ttgtctgagc cccccacggc  11460
gagagccccg ccccgttgg ccgccccaga aacagactcg cgggctcttg ccaatgggga  11520
tcgcacggtg ggcgcggcgt agccccccgtc gcccgagaac ggttacccct agcgtgccac  11580
ccgcgccgca tcggggcag aggcccggtg ggggctgggg cgccatgcgc gtgcgcgctg  11640
gtcctttggg tccggccac ccccgacccc gcggtacgcg cacgcgcgac caggaaaccc  11700
cgctaactgc gtgcgcgctg ggaattggcg ctaattgcgc gtgcgcgctg gcgattgacg  11760
```

```
cacgcgcgac ccttaaccgc gattaacgcg cacgcgcgac ggactcaatg gcgctaatcg    11820
cgcgtgcgtt ctgggcccg ggcgcttgcg cctgagttac cgcgattagc gcgcacgcaa     11880
gaccccgggc ccgcgaacgc ccacttcctg cccgagccgc tggcgcccga gggtgtggcc    11940
gctgcgtgcg ggtgaaggac gggctcggcg accgcgggct cccacaccgg cgacgcacgc    12000
cgcgcgcgac ccggtcgctg tttgaaccgg gcggaggcgg ggctggcgcc gcgcgcgctg    12060
ggccagcgac aaacttggcc cgcctccgcc cgaccgcgg cggttgggag ggggttgggg     12120
cctggcttcc tgccgcgcgc cgcggggacg gccaaccctc ccccaacccc ggaccgaagg    12180
acggcgcgcg gcgcccctgc cctccgacca gtgtttgcct tttatggtaa taacgcggcc    12240
ggcccggctt ggaggctggt cacaaacgga aataccatt attgcgccgg ccgggccgaa     12300
cctttgtccc caatctgggc gcgcgccggc gccccctggc ggcctaagga ggaaacaggg    12360
gttagacccg cgcgcggccg cggggaccg ccggattcct ctcggcgcgc cggaagtggc     12420
cagggcgggg gcgacttcgg ctcacagcgc gagccgcgcg gccttcaccg gtcccgcccc    12480
cgctgaagcc gagtgtcgcg gcccggctat tctcgcagct caccatgccg gtcgccacca    12540
tgataccgtc cgggccgata agagcgtcga gtggtacggc cagcggtggt actatggcag    12600
gacctg                                                              12606

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
gcggtaccaa gggcattctg aagttaacc                                     29

<210> SEQ ID NO 4
<211> LENGTH: 16
<212> TYPE: DNA
<213> ORGANISM: Artificial Sequence
<220> FEATURE:
<223> OTHER INFORMATION: Primer

<400> SEQUENCE: 4
agctccacag gcctgg                                                   16

<210> SEQ ID NO 5
<211> LENGTH: 13
<212> TYPE: DNA
<213> ORGANISM: Artificial Sequence
<220> FEATURE:
<223> OTHER INFORMATION: Oligonucleotide

<400> SEQUENCE: 5
aacaattggc ggc                                                      13

<210> SEQ ID NO 6
<211> LENGTH: 13
<212> TYPE: DNA
<213> ORGANISM: Artificial Sequence
<220> FEATURE:
<223> OTHER INFORMATION: Oligonucleotide

<400> SEQUENCE: 6
gccaattgtt gcc                                                      13
```

```
<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7
acgcgtcgac ggaaggagac aataccggaa g                              31

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ccgctcgagt tggggtgggg gaaaaggaa                                 29

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cgggatccgc ctgagaaagg aagtgagctg                                30

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
gaagatctgg aggaatgagc tggccctta                                 29

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
ctcgagttat taatagtaat caattacggg gtcat                          35

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
gtcgacgatc tgacggttca ctaaaccagc tct                            33
```

POLYNUCLEOTIDE

CROSS-REFERENCE TO RELATED APPLICATIONS

This application claims priority under 35 U.S.C. §119(a) to U.K. Application No. GB0022995.5, filed Sep. 20, 2000, and claims priority under 35 U.S.C. §119(e) to U.S. Provisional Application Ser. No. 60/252,048, filed Nov. 20, 2000. All applications are hereby incorporated by reference in their entireties.

FIELD OF THE INVENTION

The present invention relates to a polynucleotide comprising a ubiquitous chromatin opening element (UCOE) that does not occur in nature. The present invention also relates to a vector comprising the polynucleotide sequence, a host cell comprising the vector and use of the polynucleotide, vector or host cell in therapy, or for in vitro protein expression applications.

BACKGROUND OF THE INVENTION

The current model of chromatin structure in higher eukaryotes postulates that genes are organized in "domains" (Dillon & Grosveld, 1994, Curr. Opin. Genet. Dev. 4:260–264; Higgs, 1998, Cell, 95:299–302, each of which is incorporated herein by reference). Chromatin domains are envisaged to exist in either a condensed, "closed", transcriptionally silent state, or in a de-condensed, "open" and transcriptionally competent configuration. The establishment of an open chromatin structure characterized by increased DNAseI sensitivity, DNA hypomethylation and histone hyperacetylation, is considered a pre-requisite to the commencement of gene expression.

The open and closed nature of chromatin regions is reflected in the behaviour of transgenes that are randomly integrated into the host cell genome. Identical constructs give different patterns of tissue-specific and development stage-specific expression when integrated at different locations in the mouse genome (Palmiter & Brinster, 1986, Ann. Rev. Genet., 20:465–499; Allen, et al., 1988, Nature, 333:852–855; Bonnerot, et al., 1990, Proc. Natl. Acad. Sci. USA, 87:6331–6335, each of which is incorporated herein by reference). A variegated expression pattern within a given transgenic mouse tissue, known as position effect variegation (PEV), is also frequently observed (Kioussis & Festenstein, 1997, Curr. Opin. Genet. Dev., 7:614–619, which is incorporated herein by reference). When exogenous genes are integrated into the chromosome of mammalian cells cultures in vitro, many of the integration events result in rapid silencing of the transgene and the remainder give large variability in expression levels (Pikaart et al., 1998, Genes Dev., 12:2852–2862; Fussenegger, et al., 1999, Trends Biotech., 17:35–42, each of which is incorporated herein by reference). These position effects render transgene expression inefficient, with implication for both basic research and biotechnology applications.

The chromatin domain model of gene organization suggests that genetic control elements that are able to establish and maintain a transcriptionally competent open chromatin structure should be associated with active regions of the genome.

Locus Control Regions (LCRs) are a class of transcriptional regulatory elements with long-range chromatin remodelling capability. LCRs are functionally defined in transgenic mice by their ability to confer site-of-integration independent, transgene copy number-dependent, physiological levels of expression on a gene linked in cis, especially single copy transgenes (Fraser & Grosveld, 1998, Curr. Opin. Cell Biol., 10:361–365; Li et al., 1999, Trends Genet., 15:403–408, each of which is incorporated herein by reference). Crucially, such expression is tissue-specific. LCRs are able to obstruct the spread of heterochromatin, prevent PEV (Kioussis & Festenstein, 1997, supra) and consist of a series of DNAse I hypersensitive (HS) sites which can be located either 5' or 3' of the genes that they regulate (Li et al., 1999, supra).

LCRs appear to be comprised of two separate, although not necessary independent components. First, the establishment of an open chromatin domain, and second a dominant transcriptional activation capacity to confer transgene copy number dependent expression (Fraser & Grosveld, 1998, supra). The molecular mechanisms by which LCRs exert their function remain a point of contention (Higgs, 1998, supra; Bulger & Groudine, 1999, Genes Dev., 13:2465–2477; Grosveld, 1999, Curr. Opin. Genet. Dev., 9:152–157; Bender et al., 2000, Mol. Cell, 5:387–393, each of which is incorporated herein by reference).

The generation of cultured mammalian cell lines producing high levels of a therapeutic protein product is a major developing industry. Chromatin position effects make it a difficult, time consuming and expensive process. The most commonly used approach to the production of such mammalian "cell factories" relies on gene amplification induced by a combination of a drug resistance gene (e.g., DHFR, glutamine synthetase (Kaufman, 1990, Methods Enzymol., 185:537–566, which is incorporated herein by reference)) and the mainatenance of stringent selective pressure. The use of vectors containing LCRs from highly expressed gene domains, using cells derived from the appropriate tissue, greatly simplifies the procedure (Needham et al., 1992, Nucleic Acids Res., 20:997–1003; Needham et al., 1995, Protein Expr. Purif., 6:124–131, each of which is incorporated herein by reference).

However, the tissue-specificity of LCRs, although useful in some circumstances, is also a major limitation for many applications, for instance where no LCR is known for the tissue in which expression is required, or where expression in many, or all, tissues is required.

Our co-pending patent application PCT/GB99/02357 (WO 00/05393), incorporated by reference herein, describes elements that are responsible for establishing an open chromatin structure across a locus that consists exclusively of ubiquitously expressed, housekeeping genes. These elements are not derived from an LCR. The invention provides a polynucleotide comprising a ubiquitous chromatin opening element (UCOE) which opens chromatin or maintains chromatin in an open state and facilitates reproducible expression of an operably-linked gene in cells of at least two different tissue types, wherein the polynucleotide is not derived from a locus control region.

Methylation-free CpG islands are well-known in the art (Bird et al., 1985, Cell, 40:91–99, Tazi & Bird, 1990, Cell, 60:909–920, each of which is incorporated herein by reference) and may be defined as CpG-rich regions of DNA with above average (>60%) content of CpG di-nucleotides where the cytosine residues are not methylated and which extend over the 5' ends of two closely spaced (0.1–3 kb) divergently transcribed genes. These regions of DNA remain unmethylated in all tissues throughout development (Wise & Pravtcheva, 1999, Genomics, 60:258–271, which is incorporated herein by reference). They are associated with the 5' ends of all ubiquitously expressed genes, as well as an estimated 40% of genes showing a tissue restricted expression profile (Antequera & Bird, 1993, Proc. Natl. Acad. Sci. USA, 90:11995–11999; Cross & Bird, 1995, Curr. Opin, Genet. Dev. 5:309–314, each of which is incorporated herein by reference) and are known to be localized regions of active chromatin (Tazi & Bird, 1990, supra).

An "extended" methylation-free CpG island is a methylation-free CpG island that extends across a region encompassing more than one transcriptional start site and/or extends for more than 300 bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognizes and digests at the site CCGG, which is commonly found within CpG islands, but only if the central CG residues are not methylated. Therefore, PCR conducted with HpaII-digested DNA and over a region harboring HpaII sites, does not give an amplification product due to HpaII digestion if the DNA is unmethylated. The PCR will only give an amplified product if the DNA is methylated. Therefore, beyond the methylation-free region HpaII will not digest the DNA a PCR amplified product will be observed thereby defining the boundaries of the "extended methylation-free CpG island."

We have demonstrated that regions spanning methylation-free CpG islands encompassing dual, divergently transcribed promoters from the human TATA binding protein (TBP)/proteosome component-B 1 (PSMBI) and heterogenous nuclear ribonucleoprotein A2/B1 (hnRNPA2)/heterochromatin protein 1Hsγ (HP1 $^{Hs\gamma}$) gene loci give reproducible, physiological levels of gene expression and that they are able to prevent a variegated expression pattern and silencing that normally occurs with transgene integration within centromeric heterochomatin.

We have shown that methylation-free CpG islands associated with actively transcribing promoters possess the ability to remodel chromatin and are thus thought to be a prime determinant in establishing and maintaining an open domain at housekeeping gene loci.

UCOEs confer an increased proportion of productive gene delivery events with improvements in the level and stability of transgene expression. This has important research and biotechnological applications including the generation of transgenic animals and recombinant protein products in cultured cells. We have shown beneficial effects of UCOEs on expression of a cytomegalovirus-enhanced green fluorescent protein (CMV-EGFP) reporter construct and with the secreted, pharmaceutically valuable protein erythropoietin. The properties of UCOEs also suggest utility in gene therapy, the effectiveness of which is often limited by a low frequency of productive gene delivery events and an inadequate level and duration of expression (Verma & Somia, 1997, Nature, 389:239–242, which is incorporated herein by reference).

Given these significant implications and wide ranging applications, there is a desire to further optimize transgene expression levels and achieve improved stability of gene expression over a prolonged period of culture.

One particular need is to overcome the directional bias observed in some naturally-occurring UCOEs. Although UCOEs confer position-independent transcriptional enhancement on operably-linked promoters, this is, to some extent, orientation-dependent (i.e., the UCOE is significantly more effective in one orientation than the other). In some circumstances, such as an expression vector comprising two expression units transcribed divergently with a UCOE situated between them, there is an advantage in being able to obtain balanced, high-level expression from both promoters, which may not be possible with a natural UCOE. There is therefore a need for artificially-constructed UCOEs that are effective in both orientations.

SUMMARY OF THE INVENTION

The present invention provides a polynucleotide comprising a ubiquitous chromatin opening element (UCOE), which opens chromatin or maintains chromatin in an open state and facilitates reproducible expression of an operably-linked gene in cells of at least two different tissue types, wherein the nucleotide sequence of the UCOE does not occur in nature.

The present invention also provides vectors comprising any of the polynucleotides of the invention. The vectors may further comprise an expressible gene operably-linked to a promoter and the polynucleotide of the invention. The operably-linked gene may be a therapeutic nucleic acid sequence. The vectors of the present invention may be episomal or integrating. The vectors may be a plasmid or a virus.

The present invention also provides a vector comprising SEQ ID NO:1, the CMV promoter, a multiple cloning site, a polyadenylation sequence and genes encoding selectable markers under suitable control elements.

The present invention also provides a vector comprising SEQ ID NO:2, the CMV promoter, a multiple cloning site, a polyadenylation sequence and genes encoding selectable markers under suitable control elements.

The present invention also provides host cells transfected with any of the vectors of the present invention.

The present invention also provides methods of treatment comprising administering to a patient in need of such treatment a pharmaceutically effective amount of any of the polynucleotides or vectors or host cells of the invention.

The present invention also provides pharmaceutical compositions comprising any of the polynucleotides and/or the vectors and/or the host cells of the invention in combination with a pharmaceutically acceptable excipient.

The present invention also provides methods of obtaining a desired gene product comprising using the any of the polynucleotids and/or the vectors and/or the host cells of the invention in a cell culture system in order to obtain a desired gene product.

The present invention also provides methods of increasing the expression of an endogenous gene comprising inserting any of the polynucleotides of the invention into the genome of a cell in a position operably associated with the endogenous gene thereby increasing the level of expression of the gene.

The present invention also provides transgenic plants containing cells containing any of the polynucleotides of the invention.

The present invention also provides transgenic non-human animals containing cells which contain any of the polynucleotides of the invention.

The present invention also provides methods for identifying expressible genes in a non-human animal comprising inserting a construct comprising any of the polynucleotides of the invention into embryonic stem cells of the non-human animal wherein the construct only allows drug selection following insertion into expressed genes.

The present invention also provides a nucleic acid molecule comprising a DNA sequence selected from the group consisting of SEQ ID NO:1, SEQ ID NO:2, and DNA sequences which hybridize under stringent conditions to SEQ ID NO:1 or SEQ ID NO:2.

The present invention also provides an isolated nucleic acid molecule which anneals under stringent hybridization conditions to SEQ ID NO:1 or 2.

The present invention also provides methods for preparing a polypeptide comprising providing a cell transformed or transfected with any of the nucleic acid molecules of the invention, growing the cell in conditions conducive to the production of the polypeptide, and purifying the polypeptide from the cell, or its growth environment.

BRIEF DESCRIPTION OF THE DRAWINGS

FIG. 2 shows the nucleotide sequence of the PDCD2/Actin artificial UCOE NcoI fragment (SEQ ID NO:1) according to the invention.

FIG. 3a shows CET 500, comprising the PDCD2/Actin artificial UCOE upstream of the CMV promoter and a multiple cloning site suitable for insertion of the open reading frame to be expressed. In this particular embodiment the plasmid backbone is from pEGFPN-1 and carries a kanamycin/neomycin resistance gene.

FIG. 3b shows CET 501, comprising the PDCD2/actin artificial UCOE in the reverse orientation.

FIG. 7 shows the nucleotide sequence of the RNP/HP-1/actin artificial UCOE fragment (SEQ ID NO:2) according to the invention.

FIG. 8a shows CET 600, comprising the RNP/HP-1/actin artificial UCOE upstream of the CMV promoter and a multiple cloning site suitable for insertion of the open reading frame to be expressed. In this particular embodiment the plasmid backbone is from pEGFPN-1 and carries a kanamycin/neomycin resistance gene.

FIG. 8b shows CET 601, comprising the RNP/HP-1/actin artificial UCOE in the reverse orientation.

DETAILED DESCRIPTION OF THE INVENTION

Figure 1:
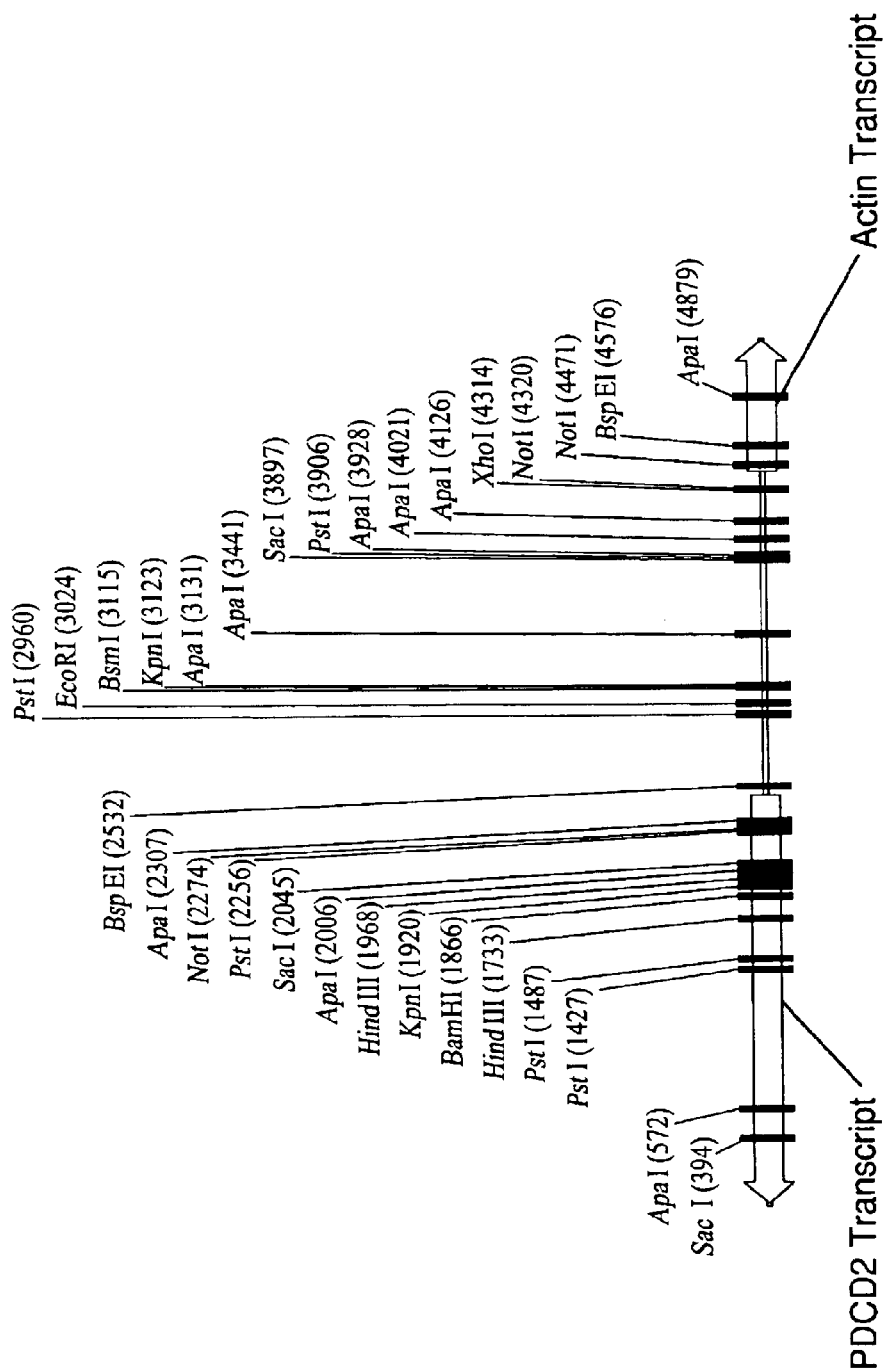
FIG. 1 is a linear restriction map of the artificial UCOE NcoI fragment. The PDCD2 and actin transcripts are shown as shaded arrows, with the direction of the arrow depicting the direction of transcription from their respective promoters.

According to the present invention there is provided a polynucleotide comprising a UCOE, which opens chromatin or maintains chromatin in an open state and facilitates reproducible expression of an operably-linked gene in cells of at least two different tissue types, wherein the nucleotide sequence of the UCOE does not occur in nature.

Genomic regions comprising regulatory sequences from at least two genes were combined to form a chimeric UCOE which significantly enhanced gene expression over a prolonged period of culture. Such a chimeric UCOE constitutes a nucleotide sequence that does not occur in nature. Accordingly the phrase "does not occur in nature" refers to a situation wherein the nucleotide sequence of the element constituting the UCOE does not naturally exist as such and is man-made or artificially constructed, being a combination of naturally-occurring and/or artificially-generated sequences.

As used herein, the terms "artificial", "artificially-constructed", "chimeric", and the like, in reference to a UCOE, are used interchangeably throughout to mean that the UCOE or the element constituting the UCOE does not naturally exist; i.e., "does not occur in nature." Where the UCOE is a combination of naturally-occurring sequences, it is their arrangement or organization into the UCOE that is non-natural. By way of non-limiting example, an artificial UCOE could be comprised of two naturally-occurring sequences that are normally disparate (from different regions of a chromosome, from different chromosomes, from different organisms, etc.) and that have been brought together in a non-natural organization, to create a chimeric or artificial UCOE.

As used herein, the terms "artificially synthesized" and "artificially-generated" in reference to sequences in a UCOE, refer to sequences that are non-natural; i.e., sequences that are not naturally-occurring and are wholly synthetic. Such "artificially synthesized" and "artificially-generated" sequences can also be combined with naturally-occurring sequences to make up or create an artificial UCOE.

According to an alternative aspect of the invention there is provided a nucleic acid molecule comprising a DNA sequence selected from:
i) the DNA sequence as represented in FIG. 2 or FIG. 7;
ii) DNA sequences which hybridize to the sequence presented in FIG. 2 or FIG. 7 which encode a polypeptide according to the invention.

In a preferred embodiment of the invention there is provided an isolated nucleic acid molecule which anneals under stringent hybridization conditions to the sequence presented in FIG. 2 or FIG. 7.

Stringent hybridization/washing conditions are well known in the art. For example, nucleic acid hybrids that are stable after washing in 0.1× SSC, 0.1% SDS at 60° C. It is well known in the art that optimal hybridization conditions can be calculated if the sequence of the nucleic acid is known. For example, hybridization conditions can be determined by the GC content of the nucleic acid subject to hybridization. See Sambrook et al., eds., Molecular Cloning: A Laboratory Manual ($2^{nd}$ ed.) Cold Spring Harbor Laboratory Press, Cold Spring Harbor, N.Y. (1989), which is incorporated herein by reference. A common formula for calculating the stringency conditions required to achieve hybridization between nucleic acid molecules of a specified homology is:

$$T_m=81.5° C.+16.6 \, Log \, [Na^+]+0.41 \, [\% \, G+C]-0.63 \, (\% \, formamide)$$

Preferably the polynucleotide of the present invention facilitates reproducible expression of an operably-linked gene non-tissue specifically.

Preferably the polynucleotide of the present invention facilitates reproducible expression of an operably-linked gene in all tissue types where active gene expression occurs.

Preferably the polynucleotide of the present invention facilitates expression of an operably-linked gene at a physiological level.

Preferably the polynucleotide of the present invention comprises an extended methylation-free, CpG-island.

Preferably the polynucleotide of the present invention comprises one or more naturally-occurring sequences associated with the control of gene expression.

Preferably the polynucleotide of the present invention comprises one or more naturally-occurring promoters.

Preferably the polynucleotide of the present invention comprises dual or bi-directional promoters that transcribe divergently.

Preferably the polynucleotide of the present invention comprises the human β-actin CpG island/promoter region, or fragment thereof.

Preferably the polynucleotide of the present invention comprises a DNA fragment within the range of 100 bp to 3 kb spanning the human β-actin CpG island/promoter region or a fragment thereof.

Preferably the polynucleotide of the present invention comprises the human PDCD2 CpG island/promoter region or a fragment thereof.

Preferably the polynucleotide of the present invention comprises a DNA fragment within the range from φbp to 3.0 kb spanning the human PDCD2 CpG island/promoter region, or a fragment thereof.

Preferably the polynucleotide of the present invention comprises a DNA fragment within the range from 100 bp to 3.0 kb spanning the human β-actin CpG island/promoter region and a DNA fragment within the range from 100 bp to 3.0 kb spanning the human PDCD2 CpG island/promoter region. Preferably said fragments are directly adjacent with their promoters oriented divergently.

Preferably the polynucleotide of the present invention comprises a 2 kb DNA fragment spanning the human β-actin CpG island/promoter region and a 1.8 kb DNA fragment spanning the human PDCD2 CpG island/promoter region. Preferably said fragments are directly adjacent with their promoters oriented divergently.

In further preferred embodiment the polynucleotide comprises the sequence of FIG. 2 or a fragment thereof, in either orientation.

Preferably the polynucleotide comprises the human RNP CpG island/promoter region or a fragment thereof.

Preferably the polynucleotide comprises a 4 kb DNA fragment spanning the human RNP CpG island/promoter region.

Preferably the polynucleotide comprises an extended methylation-free CpG island containing bidivergent promoters adjacent to at least one further sequence comprising a methylation-free CpG island.

Preferably the polynucleotide comprises the human RNP CpG island/promoter region and a DNA fragment in the range 100 bp to 3.0 kb spanning the human β-actin CpG island/promoter region.

In a further preferred embodiment the polynucleotide comprises the sequence of FIG. 7 or a fragment thereof in either orientation. Preferably the polynucleotide comprises one or more promoter sequences.

It is known in the art that initiation of transcription may, under some circumstances, be inhibited by read-through transcripts from upstream promoters (Youssoufian & Lodish, 1993, Transcriptional inhibition of the murine erythropoietin receptor gene by an upstream repetitive element, Mol. Cell. Biol., 13:98–104, which is incorporated herein by reference). Therefore, one embodiment of the invention comprises the polynucleotide of the present invention wherein one or more of the promoter sequences are mutated in such a way that they are incapable of initiating transcription.

Preferably the promoter is selected from CMV, EF-1α, RSV LTR, or HIV2 LTR or combinations of sequences derived therefrom. More preferably the promoter is a CMV promoter. Most preferably it is the mouse CMV promoter.

Preferably the polynucleotide of the present invention comprises at least one sequence which is artificially synthesized.

The present invention also provides a vector comprising the polynucleotide of the present invention.

Preferably said vector is an expression vector adapted for eukaryotic gene expression.

Typically said adaptation includes, by example and not by way of limitation, the provision of transcription control sequences (promoter sequences) which mediate cell/tissue specific expression.

Promoter and enhancer are terms well-known in the art and include the following features which are provided by example only, and not by way of limitation. Promoters are 5', cis-acting regulatory sequences directly linked to the initiation of transcription. Promoter elements include so-called TATA box and RNA polymerase initiation selection (RIS) sequences which function to select a site of transcription initiation. These sequences also bind polypeptides which function, inter alia, to facilitate transcription initiation selection by RNA polymerase.

Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors is responsive to a number of environmental cues which include, by way of example and not by way of limitation, intermediary metabolites (e.g., glucose), environmental effectors (e.g., heat). See David S. Latchman, Eukaryotic Transcription Factors, $3^{rd}$ Edition, Academic Press, San Diego (1999), which is incorporated herein by reference.

Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since they are self-replicating and so persist without the need for integration. Episomal vectors of this type are described in WO98/07876, which is incorporated herein by reference.

Adaptations which facilitate the expression of vector encoded genes include the provision of transcription termination/polyadenylation sequences. This also includes the provision of internal ribosome entry sites (IRES) which function to maximize expression of vector encoded genes arranged in bicistronic or multi-cistronic expression cassettes.

These adaptations are well-known in the art. There is a significant amount of published literature with respect to expression vector construction and recombinant DNA techniques in general. See Sambrook et al., eds., 1989, supra, and references therein; Marston, DNA Cloning Techniques: A Practical Approach, Vol. 111, IRL Press, Oxford, UK, (1987); Ausubel et al., eds., Current Protocols in Molecular Biology, John Wiley & Sons, New York, N.Y. (1994), each of which, including the references cited therein, is incorporated herein by reference.

Preferably the vector comprises an expressible gene operably-linked to a promoter and the polynucleotide.

Preferably the vector is an episomal or integrating vector.

In a preferred embodiment, the vector of the present invention is a plasmid.

Alternatively, the vector may be a virus, including, but not limited to, an adenovirus, adeno-associated virus, a herpesvirus, vaccinia virus, lentivirus or other retrovirus.

Preferably the operably-linked gene is a therapeutic nucleic acid sequence.

Preferably the vector comprises two sites for insertion of open reading frames to be expressed, each transcribed from a distinct promoter, said promoters being arranged so as to transcribe divergently and both promoters being operably-linked to an artifically-constructed UCOE situated between them, and wherein said UCOE has been so constructed as to be effective in both orientations. This is particularly useful for the production of proteins that comprise two or more polypeptide chains, including, but not limited to, immunoglobulins. The insertion sites in the vector may be inserted with nucleic acid encoding different polypeptides of interest, including, but not limited to an open reading frame encoding an immunoglobulin heavy and an immunoglobulin light chain.

Preferably the vector comprises the sequence of FIG. 2, the CMV promoter, a multiple cloning site, a polyadenylation sequence and genes encoding selectable markers under suitable control elements. It will be apparent to one of skill in the art that the UCOE can be inserted in both orientations.

Figure 3A:
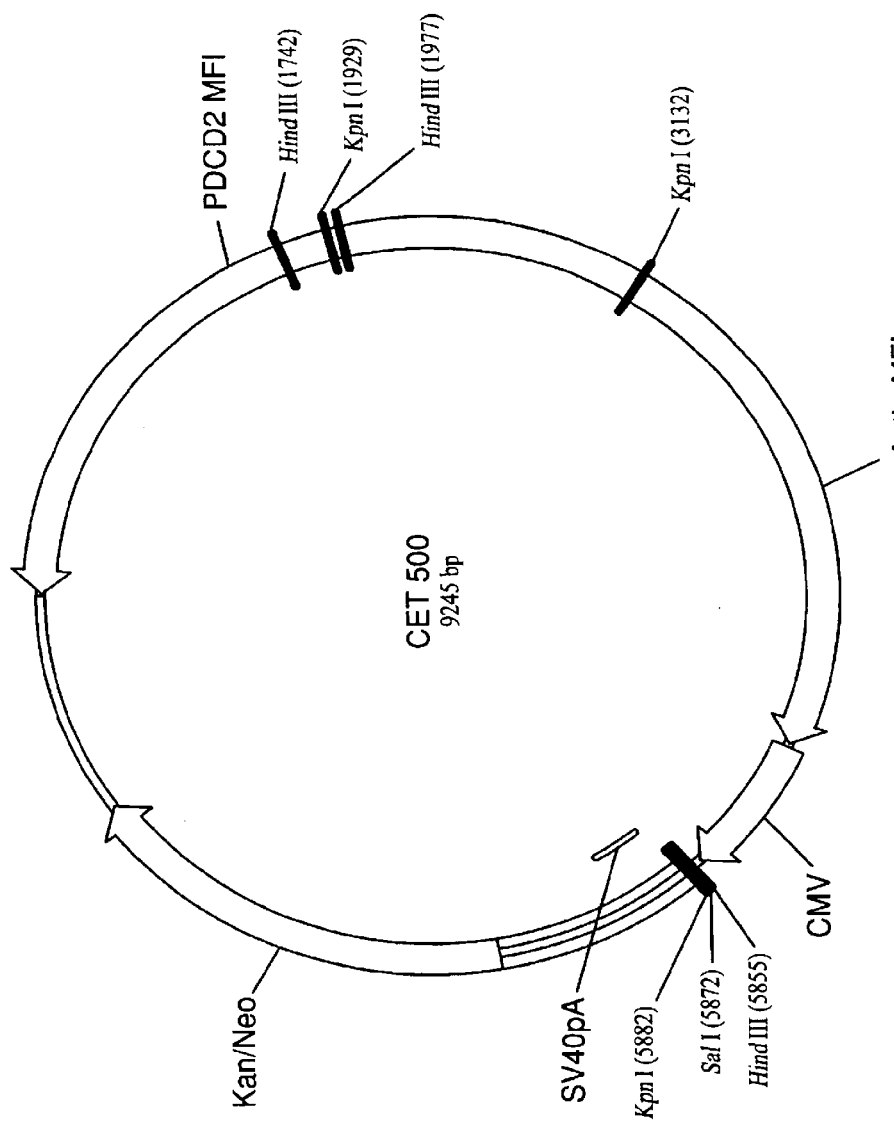
FIGS. 3a and 3b depict plasmid maps of the PDCD2/Actin artificial UCOE-containing expression vectors.

Preferably the vector comprising the artificial UCOE is CET 500 as shown schematically in FIG. 3a.

Figure 3B:
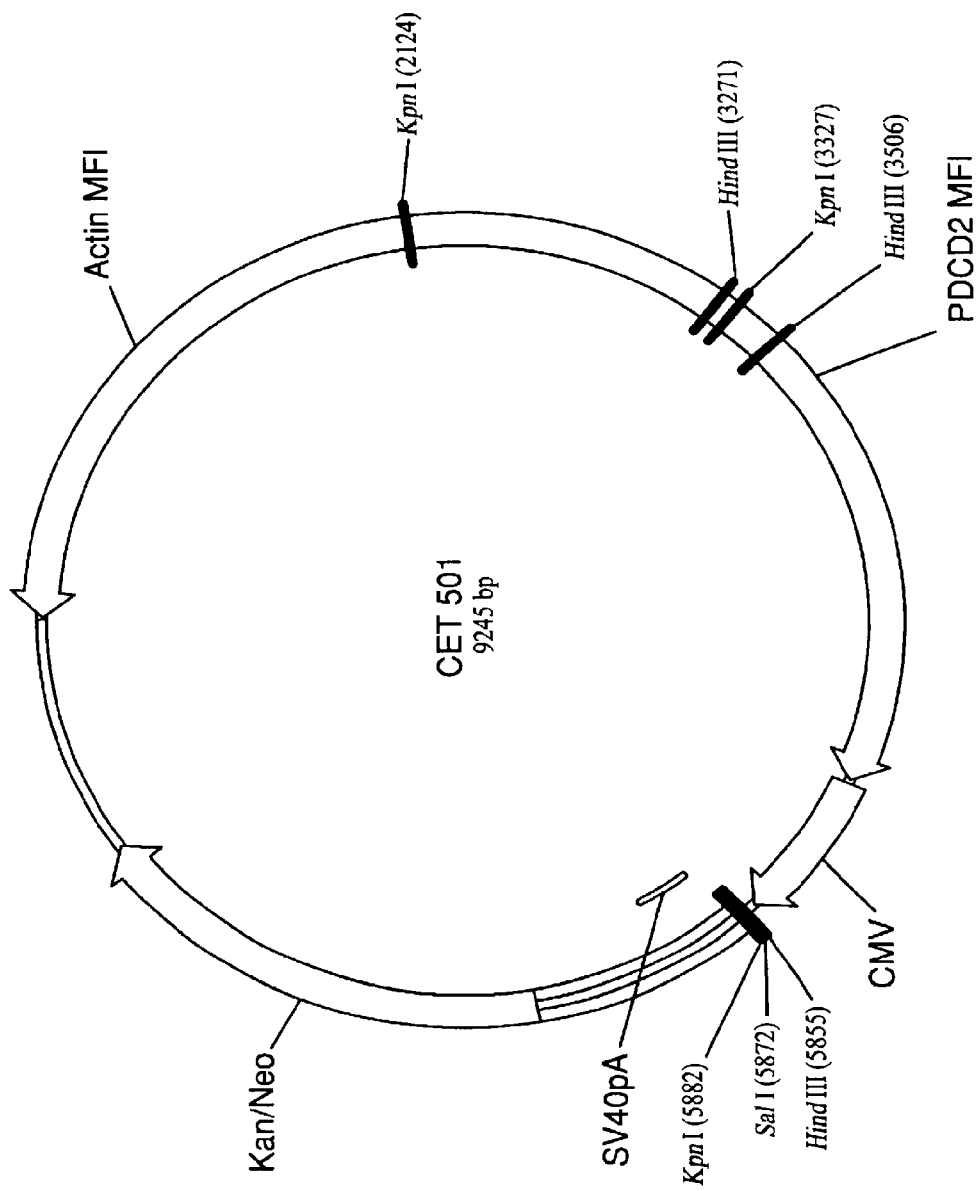

In an alternative embodiment, the vector is CET 501 as shown in FIG. 3b.

Alternatively, the vector of any of the claims comprises the sequence of FIG. 7, the CMV promoter, a multiple cloning site, a polyadenylation sequence and genes encoding selectable markers under suitable control elements. Similarly, it will be apparent to one of skill in the art that the artificial UCOE can be inserted in both orientations.

Figure 8A:
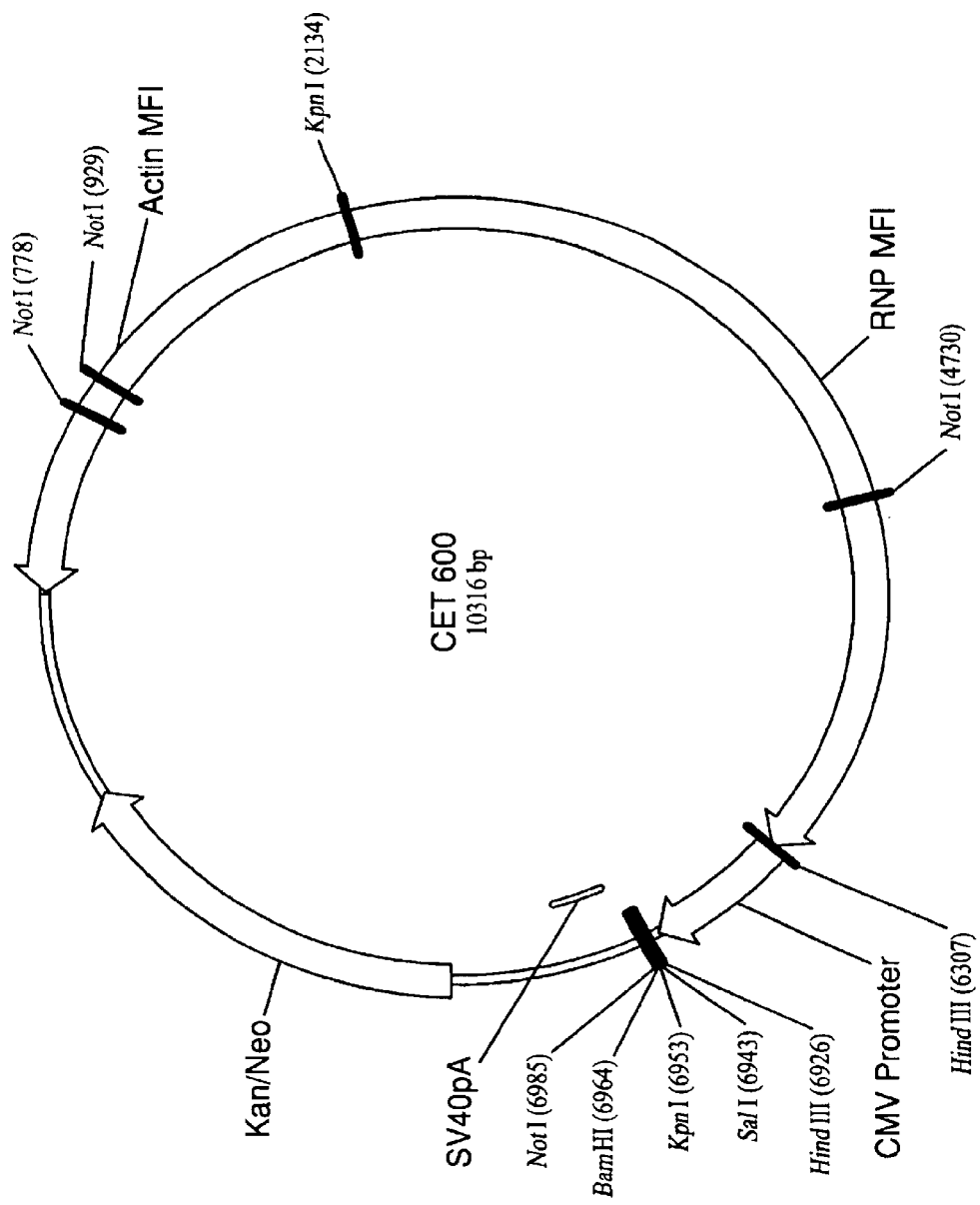
FIGS. 8a and 8b depict plasmid maps of RNP/HP-1/actin artificial UCOE-containing expression vectors.

In a preferred embodiment of this alternative, the vector comprising the artificial UCOE is known as CET 600 as shown schematically in FIG. 8a.

Figure 8B:
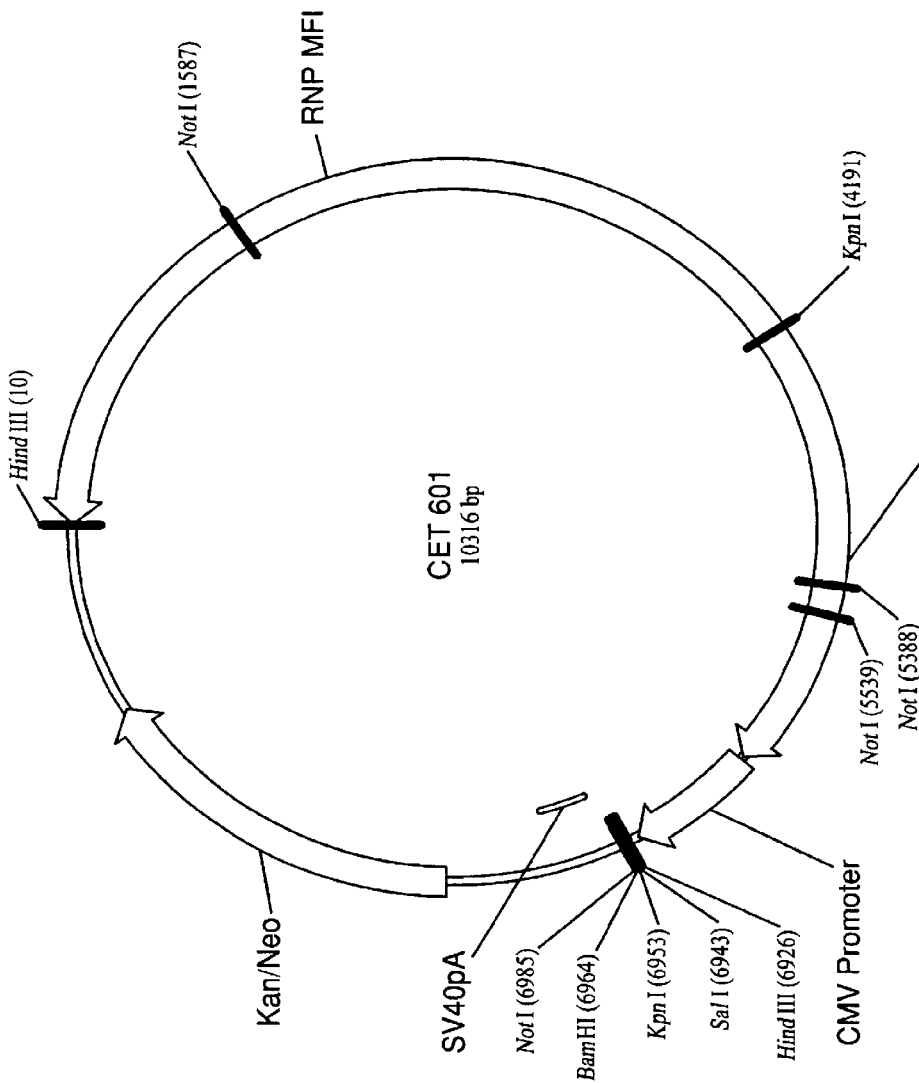

In a further alternative embodiment, the vector is CET 601 as shown schematically in FIG. 8b.

The present invention also provides a host cell that is transfected with the vector of the present invention.

The present invention also provides the polynucleotide, vector or the host cell for use in therapy.

The present invention also provides use of the polynucleotide, vector or host cell in the manufacture of a composition for use in gene therapy.

The present invention also provides a method of treatment, comprising administering to a patient in need of such treatment a pharmaceutically effective amount of the polynucleotide, vector or host cell of the present invention. Preferably the patient is suffering from a disease treatable by gene therapy.

The present invention also provides a pharmaceutical composition comprising the polynucleotide and/or the vector and/or host cell, optionally in admixture with a pharmaceutically acceptable carrier or diluent, for therapy to treat a disease or provide the cells of a particular tissue with an advantageous protein or function.

The polynucleotide, vector or host cell of the invention or the pharmaceutical composition may be administered via a route which includes systemic, intramuscular, intravenous, aerosol, oral (solid or liquid form), topical, ocular, rectal, intraperitoneal and/or intrathecal and local direct injection.

The exact dosage regime will, of course, need to be determined by individual clinicians for individual patients and this, in turn, will be controlled by the exact nature of the protein expressed by the gene of interest and the type of tissue that is being targeted for treatment.

The dosage also will depend upon the disease indication and the route of administration. The number of doses will depend upon the disease, and the efficacy data from clinical trials.

The amount of polynucleotide or vector DNA delivered for effective gene therapy according to the invention will preferably be in the range of between 50 ng –1000 µg of vector DNA/kg body weight; and more preferably in the range of between about 1–100 µg vector DNA/kg.

Although it is preferred according to the invention to administer the polynucleotide, vector or host cell to a mammal for in vivo cell uptake, an ex vivo approach may be utilized whereby cells are removed from an animal, transduced with the polynucleotide or vector, and then re-implanted into the animal. The liver, for example, can be accessed by an ex vivo approach by removing hepatocytes from an animal, transducing the hepatocytes in vitro and re-implanting the transduced hepatocytes into the animal (e.g., as described for rabbits by Chowdhury et al., 1991, Science, 254:1802–1805, which is incorporated herein by reference, or in humans by Wilson, 1992, Hum. Gene Ther., 3:179–222, which is incorporated herein by reference). Such methods also may be effective for delivery to various populations of cells in the circulatory or lymphatic systems, such as erythrocytes, T cells, B cells and haematopoietic stem cells.

In another embodiment of the invention, there is provided a mammalian model for determining the efficacy of gene therapy using the polynucleotide, vector or host cell of the invention. The mammalian model comprises a transgenic animal whose cells contain the vector of the present invention. Methods of making transgenic mice (Gordon et al., 1980, Proc. Natl. Acad. Sci. USA, 77:7380–7384; Harbers et al., 1981, Nature, 293:540–542; Wagner et al., 1981, Proc. Natl. Acad. Sci. USA, 78:5016–5020; and Wagner et al., 1981, Proc. Natl. Acad. Sci. USA, 78:6376–6380, each of which is incorporated herein by reference), sheep, pigs, chickens (see Hammer et al., 1985, Nature, 315:680–683, which is incorporated herein by reference), etc., are well-known in the art and are contemplated for use according to the invention. Such animals permit testing prior to clinical trials in humans.

Transgenic animals containing the polynucleotide of the invention also may be used for long-term production of a protein of interest.

The present invention also provides for use of the polynucleotide and/or vector and/or host cell in a cell culture system in order to obtain a desired gene product.

Suitable cell culture systems are well known in the art and are fully described in the body of literature known to those skilled in the art.

The present invention also provides for use of the polynucleotide to increase the expression of an endogenous gene comprising inserting the polynucleotide into the genome of a cell in a position operably associated with the endogenous gene thereby increasing the level of expression of the gene.

The present invention also provides the use of the polynucleotide of the present invention in producing transgenic plants.

The generation of transgenic plants which have increased yield, resistance, etc. are well known to those skilled in the art. The present invention also provides for transgenic plant containing cells which contain the polynucleotide of the present invention. Some or all of the cells comprising the artificial UCOE may originate from plants.

The present invention also provides for a transgenic non-human animal containing cells which contain the polynucleotide.

The present invention also relates to the use of polynucleotide of the present invention in functional genomics applications. Functional genomics relates principally to the sequencing of genes specifically expressed in particular cell types or disease states and now provides thousands of novel gene sequences of potential interest for drug discovery or gene therapy purposes. The major problem in using this information for the development of novel therapies lies in how to determine the functions of these genes. UCOEs can be used in a number of functional genomic applications in order to determine the function of gene sequences. The functional genomic applications of the present invention include, but are not limited to:

(1) Using the polynucleotide of the present invention to achieve sustained expression of anti-sense versions of the gene sequences or ribozyme knockdown libraries, thereby determining the effects of inactivating the gene on cell phenotype.

(2) Using the polynucleotide of the present invention to prepare expression libraries for the gene sequences, such that delivery into cells will result in reliable, reproducible, sustained expression of the gene sequences. The resulting cells, expressing the gene sequences can be used in a variety of approaches to function determination and drug discovery. For example, raising neutralising antibodies to the gene product; rapid purification of the protein product of the gene itself for use in structural, functional or drug screening studies; or in cell-based drug screening.

(3) Using the polynucleotide of the present invention in approaches involving mouse embryonic stem (ES) cells and transgenic mice. One of the most powerful functional genomics approaches involves random insertion into genes in mouse ES cells of constructs which only allow drug selection following insertion into expressed genes, and which can readily be rescued for sequencing (Hicks et al., 1997, Nature Genetics, 16:338–334, which is incorporated herein by reference). Transgenic mice with knockout mutations in genes with novel sequences can then readily be made to probe their function. At present this technology works well for the 10% of mouse genes which are well expressed in mouse ES cells. Incorporation of UCOEs into the integrating constructs will enable this technique to be extended to identify all genes expressed in mice.

In an alternative embodiment of the invention, there is provided a method for the production of the polypeptide according to the invention comprising:

i) providing a cell transformed/transfected with a nucleic acid molecule according to the invention;

ii) growing said cell in conditions conducive to the manufacture of said polypeptide; and iii) purifying said polypeptide from said cell, or its growth environment.

In a preferred embodiment of the invention said nucleic acid molecule is the vector according to the invention.

In a preferred method of the invention said vector encodes, and thus said polypeptide is provided with, a secretion signal to facilitate purification of said polypeptide.

Alternatively, other preferred embodiments may include further refinements to facilitate purification of expressed recombinant protein, such as affinity tags or epitopes, or enzymatic cleavage sites.

The invention is further illustrated by way of the following examples, with reference to the accompanying figures, which are intended to elaborate several embodiments of the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Heterologous Combinations of UCOE Fragments

We have found that the substitution of the A2/HP1 fragments in the 4.0CMV and 8.0CMV constructs with the comparable region from the TBP/B1 locus gave substantial increases in the level and stability of EGFP expression from the hCMV promoter. These findings in tissue culture cells provide evidence that regions of DNA encompassing an extended CpG island and divergently transcribed promoters are responsible for conferring an increase in the proportion of viable integration events, significantly improved transgene expression and a resistance to transcriptional silencing even from within centromeric heterochromatin.

Genomic regions encompassing CpG islands from housekeeping genes associated with a single promoter were combined. The construct comprised the 2 kb CpG island from the 5' end of the human β-actin gene (Ng et al., 1985, Mol. Cell. Biol., 5:2720–2732, which is incorporated herein by reference) joined to a 3.2 kb fragment containing the CpG island from the 5' end of the human PDCD2 gene. The promoters were divergently transcribed and their transcriptional start sites separated by 1.9 kb.

The entire 5.2 kb combination was then linked to an EGFP reporter gene driven by the CMV promoter (PDCD2/ACTIN). As a comparison, the β-actin CpG island/promoter region alone was also inserted upstream of the CMV-EGFP expression vector (ACTIN).

Materials and Methods

With particular reference to FIG. 2, the CMV promoter was removed from pEGFP-N1 by digestion with AseI and NheI followed by blunting with T4 DNA polymerase and religation to produce pΔ-EGFP-N1. A β-Actin promoter EGFP fusion was constructed by digesting MA39 (HSACCYBB) with BsmI and NcoI, isolating the appropriate fragment and blunting it with T4 DNA polymerase. This fragment was ligated into pΔ-EGFP-N1 that had been digested with AgeI, blunted with T4 DNA polymerase and then digested with SmaI. This produced an in frame fusion of the first codon of the β-Actin gene with EGFP, expression of which was driven off the β-Actin promoter/MFI (methylation free island). The construct, pActin-EGFP, was shown to express EGFP in stably transfected CHOK1 cells.

To construct a vector with bi-directional promoters and an extended methylation free island, the PDCD2 gene and some of its promoter was initially removed from pCP2–TNN (approximately 160 kb of the TBP locus in pCYPAC-2) by digestion with SwaI and BspEI and sub cloned into pBluescriptKS+ that had been digested with EcoRV and XmaI (pPDCD2-KS). As this vector did not contain the whole of the PDCD2 methylation free island, the remaining 5' region of the PDCD2 methylation free island, which also contained the promoter, was obtained by PCR from pCP2-TNN using the following primers 5'-GCGGTACCAAGGGCATTCTGAAGTTAACC-3' (SEQ ID NO:3), 5-AGCTCCACAGGCCTGG-3' (SEQ ID NO:4). The PCR product was then digested with KpnI (site generated with PCR primers) and StuI (internal site), pActin-EGFP was digested with SalI and KpnI, and the PDCD2 gene was removed from pPDCD2-KS by digestion with SalI and StuI. All three fragments were ligated together to create pPDCD2-Actin-EGFP.

The region containing the methylation free island of pF-PDCD2-Actin-EGFP was removed as an NcoI fragment (approximately 5.2kb), this was blunted with T4 DNA polymerase and then ligated, in both orientations, into pEGFPN-1 that had been digested with Ase I and then blunted. These vectors were called CET 510 (UCOE in forward orientation) and CET511 (UCOE in reverse orientation). The corresponding empty expression vectors with no transgene inserted into the multiple cloning sites were termed CET 500 and CET 501, respectively (see FIG. 3).

Constructs were linearized with PvuI, transfected into CHO-K1 cells and selected under G418 selection (0.6 mg/ml) for both experiments.

It will be understood that one of skill in the art may adapt these procedures for preparation and testing of other polynucleotides of the invention.

Results

Figure 4:
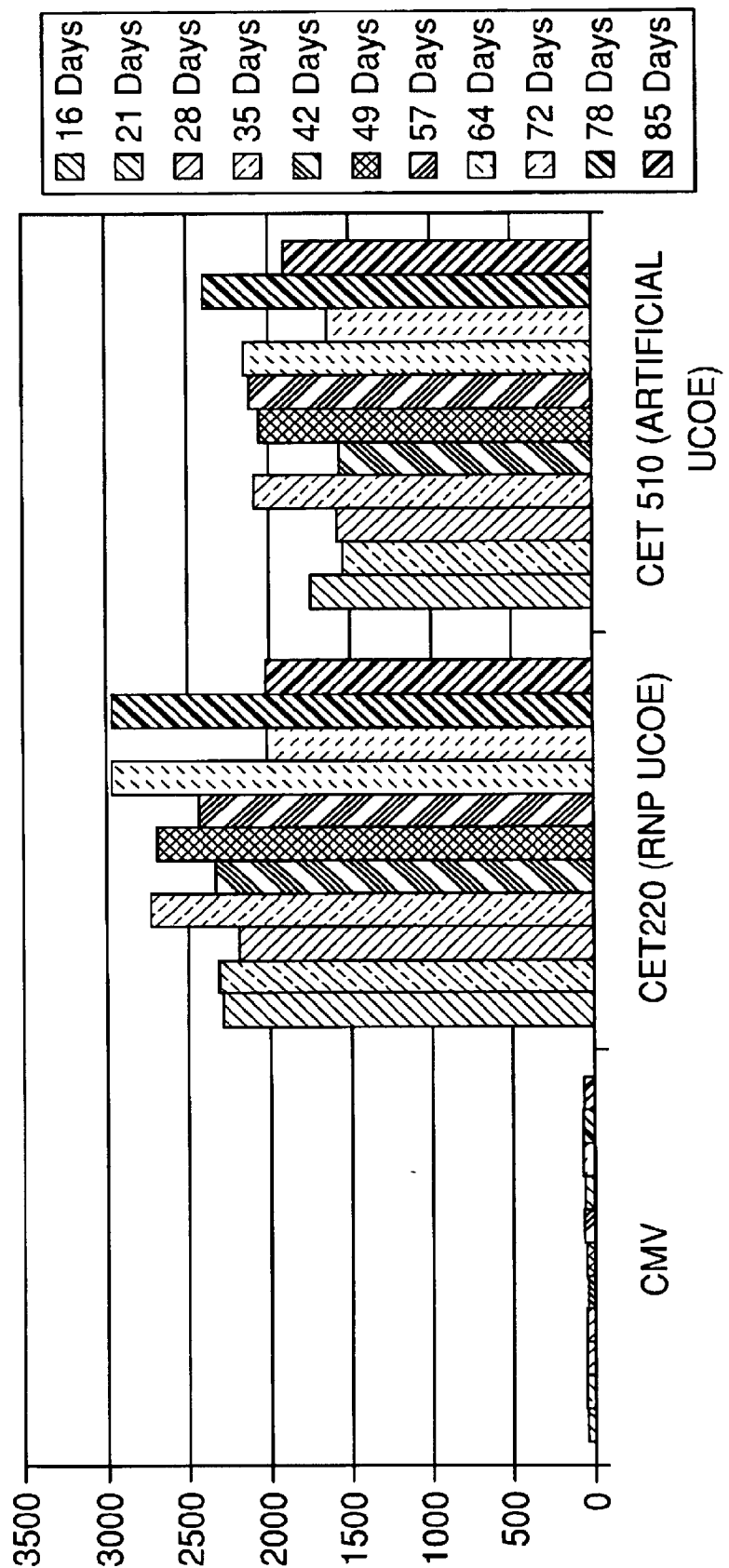
FIG. 4 shows levels of expression of a reporter transgene (EGFP) in pools of stably-transfected CHO cells maintained under G418 selection over a period of 85 days. Expression was driven by the CMV promoter alone (CMV), or in combination with the 8kb RNP/HP-1 UCOE (CET 220) or PDCD2/actin artificial UCOE (CET 510) and was measured as median fluorescence by fluorescence activated cell sorting (FACS).
Figure 5:
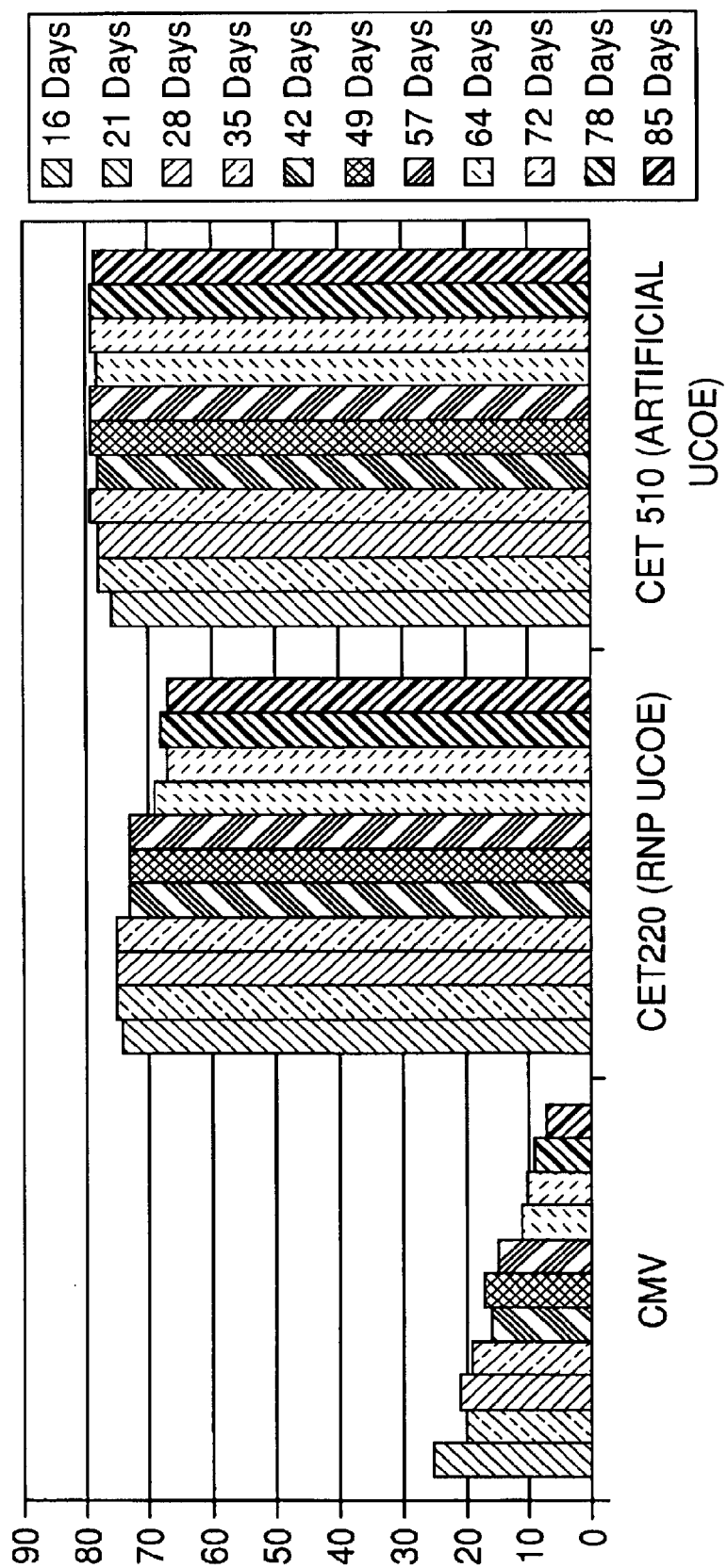
FIG. 5 shows the proportion of cells expressing the transgene in the above experiment (FIG. 4) expressed as % positive cells on FACS analysis over a period of 85 days.
Figure 6:
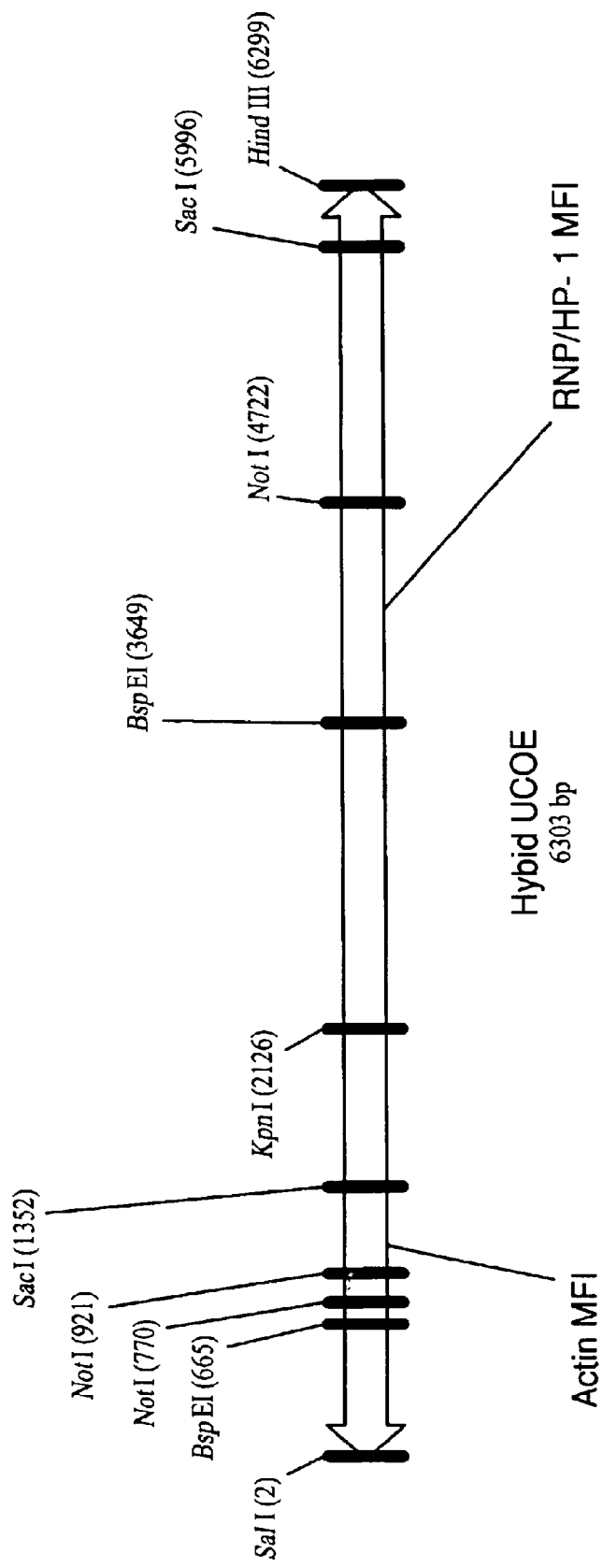
FIG. 6 is a linear restriction map of the RNP/HP-1/actin artificial UCOE fragment. The methylation-free CpG islands are shown as shaded arrows, with the direction of the arrow depicting the direction of transcription from their respective promoters.

As shown in FIGS. 4 and 5, the artificial UCOE construct gave levels of reporter gene expression that were comparable with those achieved with the 8 kb RNP/HP-1 UCOE in terms of median fluorescence, and slightly better in terms of the proportion of cells expressing over the time course of the experiment.

Example 2

Heterologous Combinations of UCOE and Methylation-Free CpG Island Fragments

Materials and Methods

The actin methylation-free island was removed from pActin-EGFP by digestion with NcoI, blunted followed by digestion with KpnI. The RNP 4 kb fragment was removed from CET 20 by digestion with KpnI and HindIII. These two fragments were then ligated into pBKS which had been digested with ClaI, blunted and then cut with HindIII. This gave the artificial UCOE in pBKS.

The artificial UCOE was then removed from pBKS by digestion with SalI and HindIII, blunted and ligated into pEGFP-N1 that had been digested with AseI and blunted. The UCOE was inserted in both orientations to create CET 610 and CET 611 respectively. The corresponding expression vectors with no transgene inserted into multiple cloning sites were termed CET 600 and CET 601, respectively (see FIG. 8).

Constructs were linearized and transfected into CHO-K1 cells and selected under G418 selection (0.6 mg/ml) for the duration of the experiments.

Results

Figure 9:
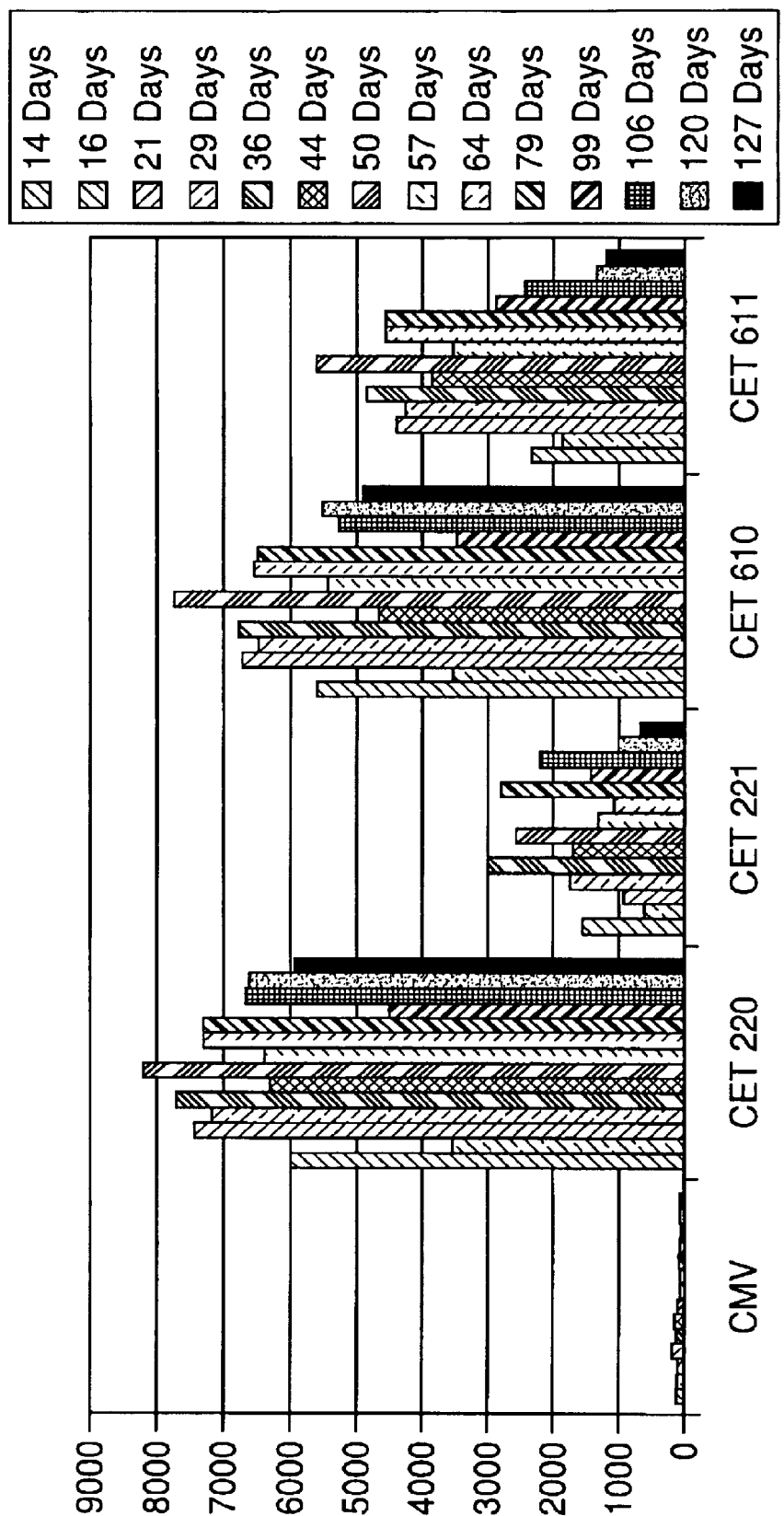
FIG. 9 shows levels of expression of a reporter transgene (EGFP) in pools of stably-transfected CHO cells maintained under G418 selection over a period of 127 days. Expression was driven by the CMV promoter alone (CMV), or in combination with the 8 kb RNP UCOE in either forward (CET 220) or reverse (CET 221) or by RNP/HP-1/actin artificial UCOE in either forward (CET 610) or reverse (CET 611) orientation and was measured as median fluorescence by FACS. It will be understood that CET 610 is therefore the equivalent of CET 600, but containing EGFP as the inserted gene, and that CET 611 is the corresponding EGFP-containing equivalent of CET 601.
Figure 10:
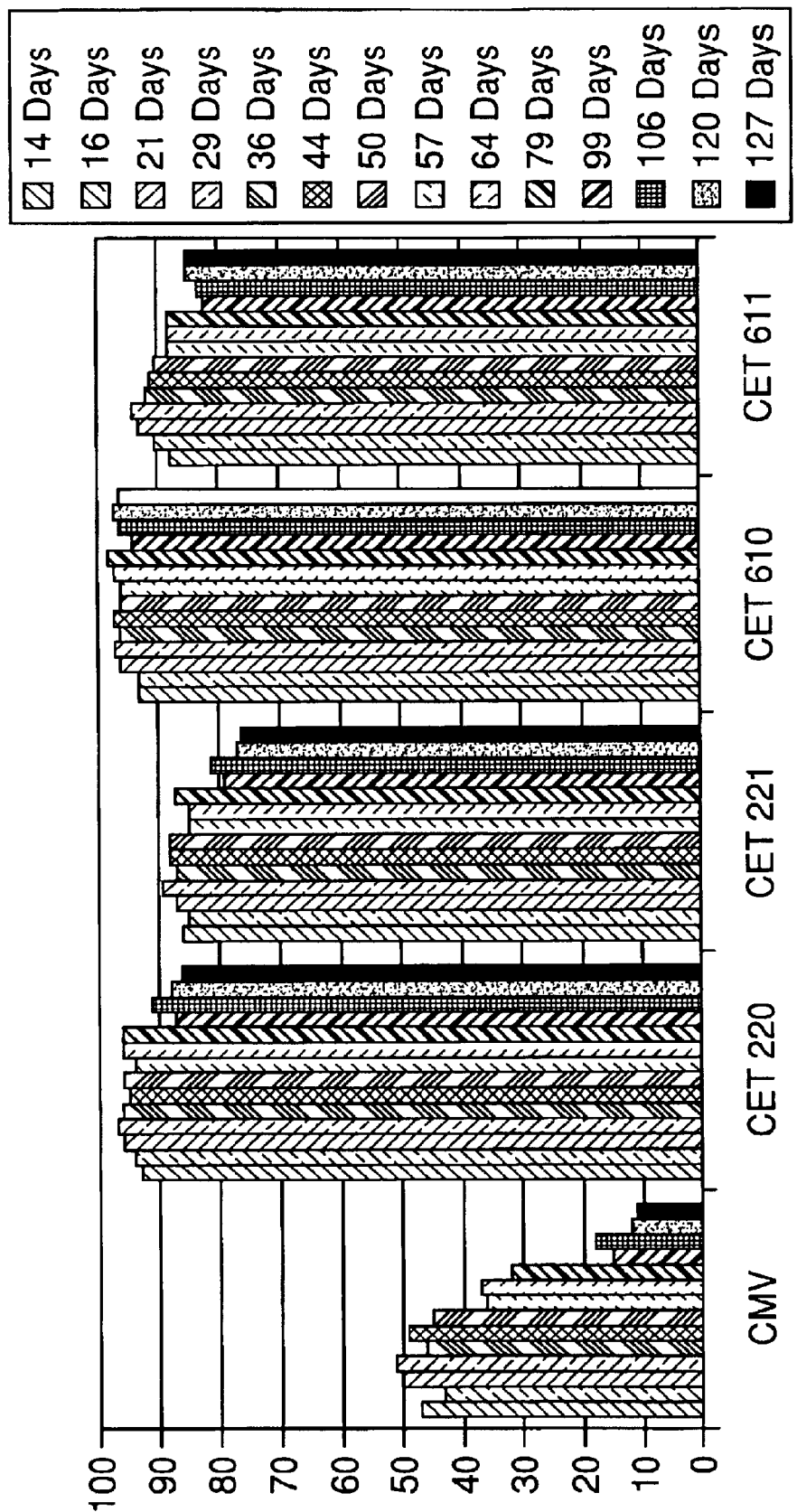
FIG. 10 shows the proportion of cells expressing the transgene in the above experiment (FIG. 9) expressed as % positive cells on FACS analysis over a period of 127 days.
Figure 11A:
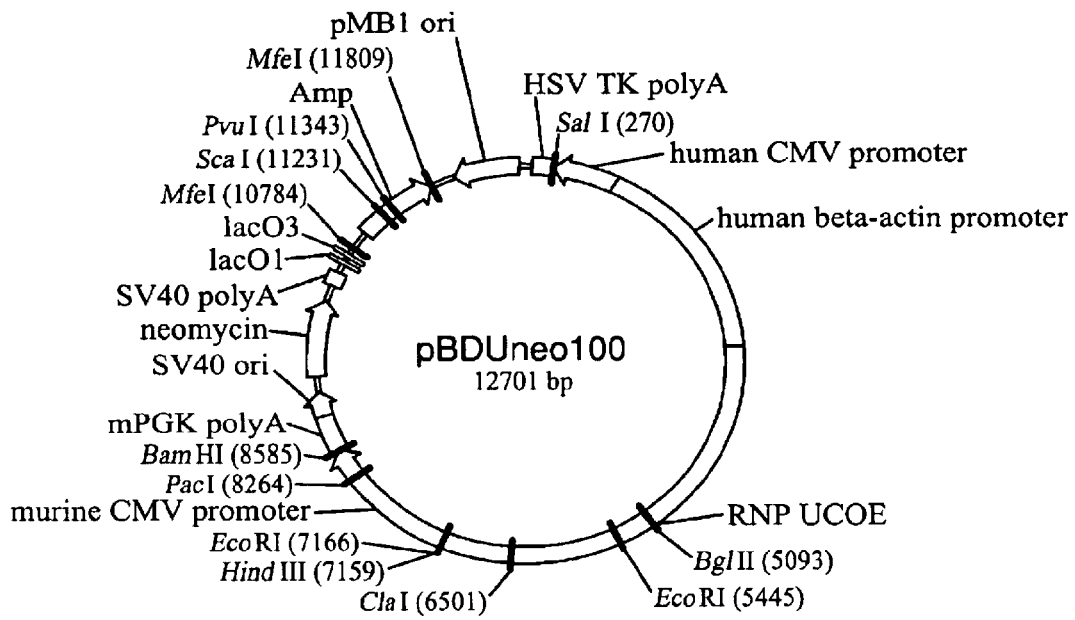
FIGS. 11a–11d depict plasmid maps of the bi-directional UCOE vectors for the expression of immunoglobulins.
Figure 11B:
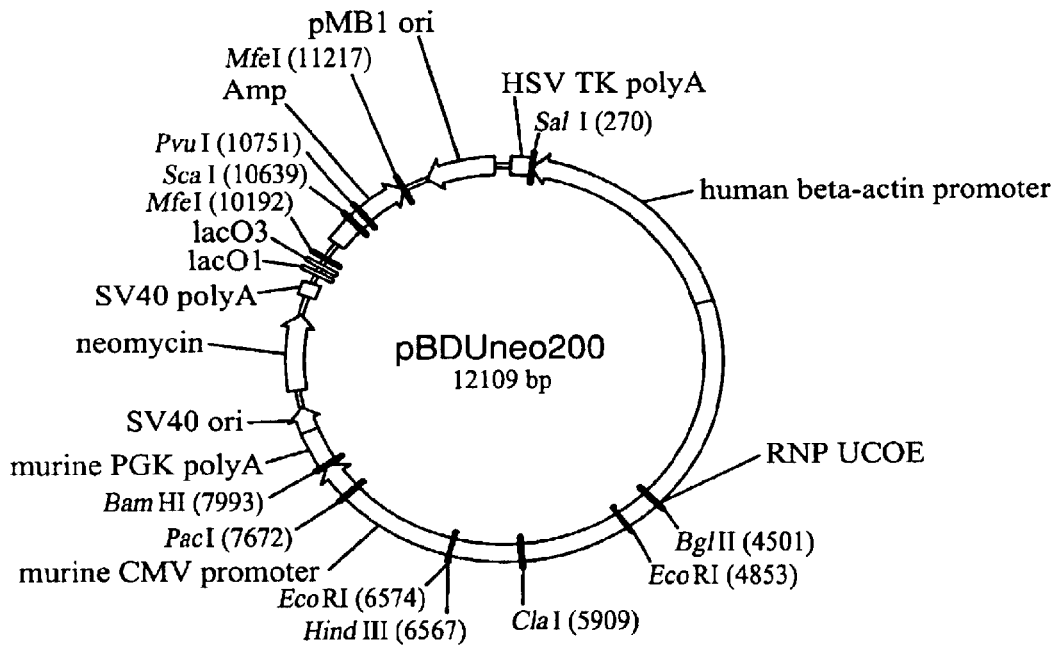
Figure 11C:
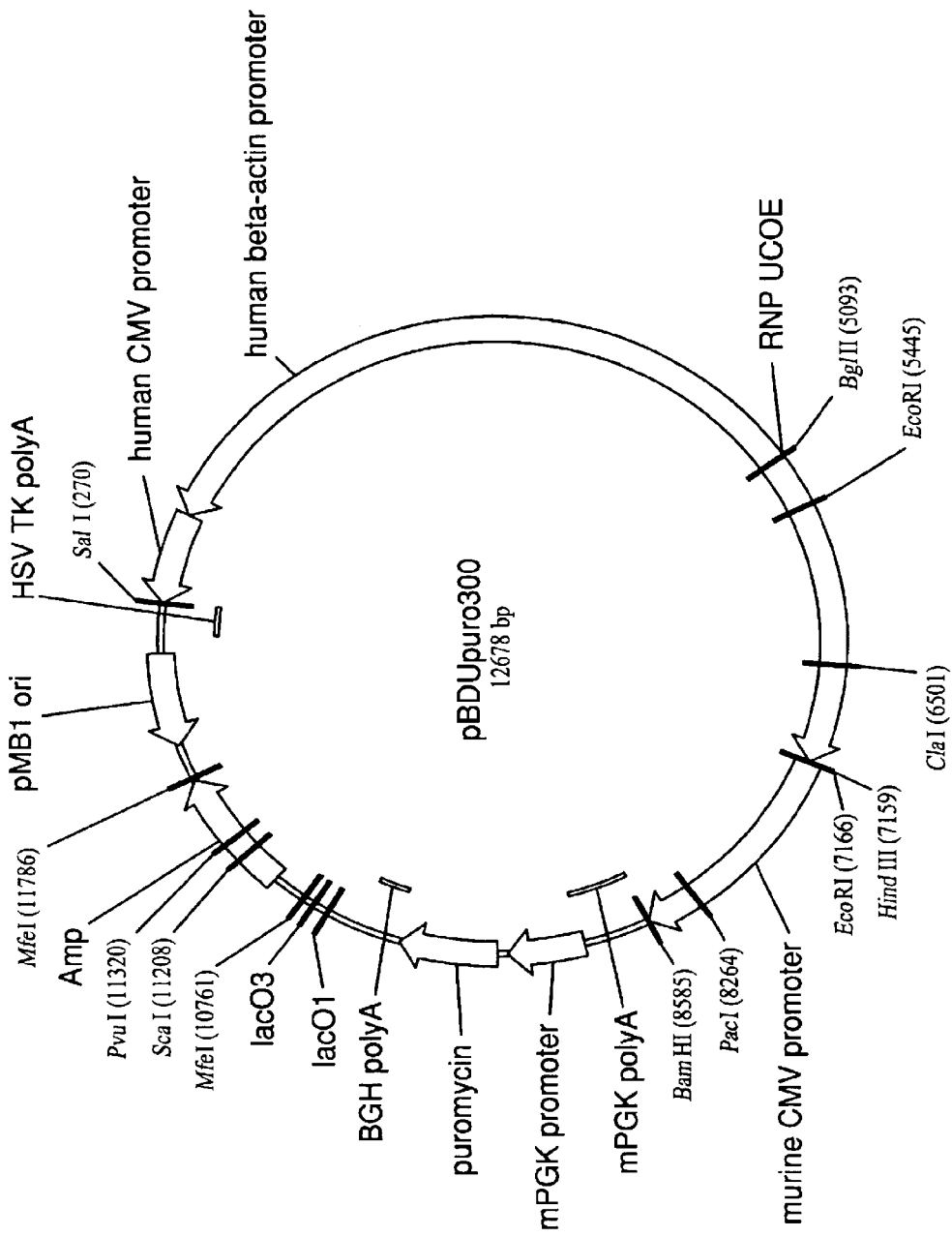
Figure 11D:
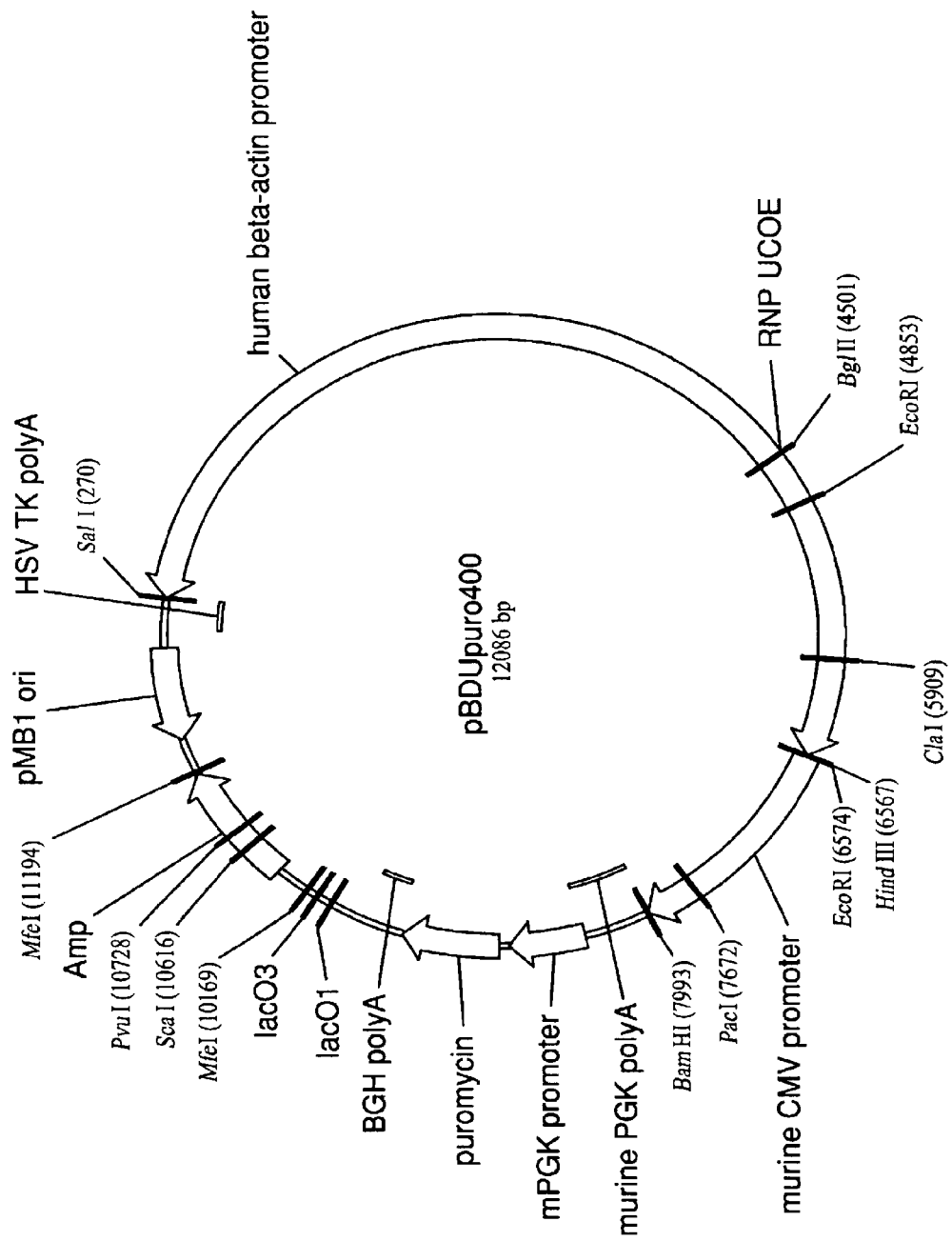

The effects of the artificial UCOE (in both orientations) on levels of transgene expression were assessed by comparison with results obtained with CMV promoter alone, and the 8 kb RNP/HP-1 UCOE (in both orientations). FIG. 9 shows that, in terms of median fluorescence on FACS analysis, the CMV promoter alone gave very low levels of expression. Both the RNP UCOE (CET 220) and artificial UCOE (CET 600) gave greatly increased (30-fold) expression in the forward orientation and were comparable. However, a directional bias seen with the RNP UCOE was less marked with the artificial UCOE, i.e., in the reverse orientation the artificial UCOE was superior, although still slightly less good than either UCOE in the forward orientation. This was true for both overall level of expression and ability to maintain expression over a prolonged period (more than 120 days).

When the same experiment was analysed in terms of proportion of cells maintaining expression over time, both UCOEs, in both orientations, gave consistently better results than CMV alone (approximately twice as many cells expressing in the early part of the experiment). This difference became more marked over longer periods, with the CMV only population progressively losing expressing cells, until by 120 days only approximately 10% cells were still expressing. This contrasts with maintenance at approximately 90% for both UCOEs in the forward orientation, and only slightly lower levels (75–85%) for the reverse orientations by the end of the experiment.

Example 3

Co-Expression of Two Genes on the Same Vector

Efficient functional antibody production requires appropriately balanced expression of the heavy and light chains. Transfection of the two chains on separate plasmids makes the maintenance of an equal copy number difficult and provides the potential for transcriptional interference between the genes if the vectors integrate close to one another in the genome. Therefore, a series of new vectors for the co-expression of two genes on the same vector have been constructed to compare neo versus puro as resistance markers and hCMV, beta actin or mCMV promoters to drive light or heavy chain expression (FIGS. 11a, 11b, 11c, and 11d).

Materials and Methods

The two SfiI sites of pORT1 (Cobra) were changed to MfeI sites by introduction of adapter molecules comprised of annealed oligos Mfe.F, 5'-AACAATTGGCGGC-3' (SEQ ID NO:5) and Mfe.R, 5'-GCCAATTGTTGCC-3' (SEQ ID NO:6). The HSV TK polyA site was amplified from pVgRXR (Invitrogen) with primers TK.F, 5'-ACGCGTCGACGGAAGGAGACAATACCGGAAG-3' (SEQ ID NO:7) and TK.R, 5'-CCGCTCGAGTTGGGGTGGGGAAAAGGAA-3' (SEQ ID NO:8), and the SalI to XhoI fragment was inserted into the SalI site. Following this, the murine PGK polyA site was amplified from male BALB/c genomic DNA (Clontech) using primers mPGK.F, 5'-CGGGATCCGCCTGAGAAAGGAAGTGAGCTG-3' (SEQ ID NO:9) and mPGK.R, 5'-GAAGATCTGGAGGAATGAGCTGGCCCTTA-3' (SEQ ID NO:10), and the BamHI to BglII fragment was cloned into the BamHI site. The AseI to SalI fragment of pcDNA3.1 containing the neo expression cassette was treated with T4 DNA polymerase, ligated to SpeI linkers (5'-GACTAGTC-3') and the SpeI fragment was then cloned into the SpeI site to give pORTneoF; or the EcoRI to NotI fragment of CET 700 (Cobra) carrying the puromycin resistance cassette was treated with T4 DNA polymerase, ligated to XbaI linkers, and the XbaI fragment was cloned into the XbaI site to give pORTpuroF.

The HindIII to BamH I murine CMV promoter fragment from pCMVEGFPN-1 (Cobra) was subcloned into the HindIII to BamHI sites of the Hybrid UCOE in BKS+ (Cobra). The human CMV promoter was then amplified from plasmid pIRESneo (Clontech) using primers hCMVF, 5'-CTCGAGTTATTAATAGTAATCAATTACGGGGTCAT-3' (SEQ ID NO:11) and hCMVR, 5'-GTCGACGATCTGACGGTTCACTAAACCAGCTCT-3' (SEQ ID NO:12) and the XhoI to SalI fragment was cloned into the SalI site. The BamHI to SalI fragment was then cloned into the BamHI to SalI sites of pORTneoF to give pBDUneo100, or into pORTpuroF to give pBDUpuro300.

The two ATG codons upstream of the SalI cloning site in the Hybrid UCOE in BKS+ were altered by site-directed mutagenesis, then the BamHI to SalI fragment was cloned into the BamHI to SalI sites of pORTneoF to give pBDUneo200, or into pORTpuroF to give pBDUpuro400.

Human antibody light chain coding sequences were cloned into either the BamHI or SalI sites of all four bi-directional UCOE vectors (pBDUneo100, pBDUneo200, pBDUpuro300 and pBDUpuro400), followed by immunoglobulin heavy chain coding sequence at the remaining BamHI or SalI cloning site to give pBDUneo112, pBDUneo121, pBDUneo212, pBDUneo221, pBDUpuro112, pBDUpuro121, pBDUpuro212 and pBDUpuro221. All eight antibody expression constructs were transfected into CHO-K1 cells using Lipofectamine® (Invitrogen) following the manufacturer's instructions, and selected with 500 µg/ml G418 (neo vectors) or 12.5 g/ml puromycin (puro vectors).

Results

CHO-K1 cells were transfected with either G418 or puromycin-resistant bidirectional UCOE vectors which express antibody. Pools were selected and antibody production rates compared between the different constructs to determine the optimal promoter and selectable marker combination for antibody expression in CHO cells. Results (Table 1) demonstrated that vectors containing the light chain expressed from the murine CMV promoter gave the best expression of the antibody. No significant difference was observed between production rates obtained with vectors containing the G418 or puromycin-resistance cassettes. The production rate from the pool of a co-transfection experiment performed separately is compared. Clones from this pool were isolated with production rates of 3–18 pg/cell/day. However, clones above 5 pg/cell/day were unstable and rapidly decreased in expression or stopped producing. Clones expressing approximately 5 pg/cell/day were used for initial fermentation experiments. These preliminary indications are very encouraging that higher production rates will be observed in clones isolated from the bi-directional UCOE vector transfectants.

TABLE 1

Expression of hAb1 (IgG4) from Bidirectional UCOE vectors (CHO-K1 pools)

| CHO-K1 POOLS Vector | H3 Promoter | K1 Promoter | Production Rate (pg/cell/day) |
|---|---|---|---|
| pBDUneo112 | murine CMV | human CMV | 0.3 |
| pBDUneo121 | human CMV | murine CMV | 1.5 |
| pBDUneo212 | murine CMV | human beta-actin | 0.06 |
| pBDUneo221 | human beta-actin | murine CMV | 1.3 |
| pBDUpuro312 | murine CMV | human CMV | 0.5 |
| pBDUpuro321 | human CMV | murine CMV | 1.4 |
| pBDUpuro412 | murine CMV | human beta-actin | 0.05 |
| pBDUpuro421 | human beta-actin | murine CMV | 2.3 |
| Co-transfecfion** | human CMV | human CMV | 0.7 |

**Co-transfection was carried out previously using the same antibody genes each driven from 4kb UCOE CMV vectors (hygro and neo selection).

The foregoing examples are meant to illustrate the invention and not to limit it in any way. Those of skill in the art will recognize modifications within the spirit and scope of the invention as set forth in the claims.

All references cited herein are hereby incorporated by reference in their entireties.

REFERENCES

1. Dillon, N. & Grosveld, F. Chromatin domains as potential units of eukaryotic gene function. *Curr. Opin. Genet. Dev.* 4, 260–264 (1994).
2. Higgs, D. R. Do LCRs open chromatin domains? *Cell* 95, 299–302 (1998).
3. Palmiter, R. D. & Brinster, R. L. Germline transformation of mice. *Ann. Rev. Genet.* 20, 465–499 (1986).
4. Allen, N. D. et al. Transgenes as probes for active chromosomal domains in mouse development. *Nature* 333, 852–855 (1988).
5. Bonnerot, C., Grimber, G., Briand, P. & Nicolas, J. F. Patterns of expression of position-dependent integrated transgenes in mouse embryo. *Proc. Natl. Acad. Sci. USA* 87:6331–6335 (1990).
6. Kioussis, D. & Festenstein, R. Locus control regions: overcoming heterochromatin-induced gene inactivation in mammals. *Curr. Opin. Genet. Dev.* 7, 614–619 (1997).
7. Pikaart, M. J., Recillas-Targa, F. & Felsenfeld, G. Loss of transcriptional activity of a transgene is accompanied by DNA methylation and histone deacetylation and is prevented by insulators. *Genes Dev.* 12, 2852–2862 (1998).
8. Fussenegger, M., Bailey, J. E., Hauser, H. & Mueller, P.P Genetic optimization of recombinant glycoprotein production by mammalian cells. *Trends Biotech.* 17, 35–42 (1999).
9. Fraser, P. & Grosveld, F. Locus control regions; chromatin activation and transcription. *Curr. Opin. Cell Biol.* 10, 361–365 (1998).
10. Li, Q., Harju, S. & Peterson, K. R. Locus Control Regions: coming of age at a decade plus. *Trends Genet.* 15: 403–408 (1999). 11. Bulger, M. & Groudine, M. Looping versus linking: toward a model for long-distance gene activation. *Genes Dev.* 13, 2465–2477 (1999).
12. Grosveld, F. Activation by locus control regions? *Curr. Opin. Genet. Dev.* 9 152–157 (1999).
13. Bender, M. A., Bulger, M., Close, J. & Groudine, M. β-globin Gene Switching and dnase I Sensitivity of the Endogenous β-globin Locus in Mice Do Not Require the Locus Control Region. *Mol. Cell* 5, 387–393 (2000).
14. Ortiz, B. D., Cado, D., Chen, V., Diaz, P. W. & Winoto, A. Adjacent DNA elements dominantly restrict the ubiquitous activity of a novel chromatin-opening region to specific tissues. *EMBO J.* 16, 5037–5045 (1997).
15. Ortiz, B. D., Cado, D. & Winoto, A. A new element within the T-cell receptor alpha locus required for tissue-specific locus control region activity. *Mol. Cell. Biol.* 19, 1901–1909 (1999).
16. Antequera, F. & Bird, A. Number of CpG islands and genes in human and mouse. *Proc. Natl. Acad. Sci. USA* 90, 11995–11999 (1993).
17. Cross, S. H. & Bird, A. P. CpG islands and genes. *Curr. Opin, Genet. Dev.* 5, 309–314 (1995).
18. Tazi, J. & Bird, A. Alternative chromatin structure at CpG islands. *Cell* 60, 909–920 (1990).
19. Imbert, G., Trottier, Y., Bechmann, J., & Mandel, J. L. The gene for the TATA binding protein (TBP) that contains a highly polymorphic protein coding CAG repeat maps to 6q27. *Genomics* 21: 667–668 (1994).
20. Purrello, M. et al. Physical mapping at 6q27 of the locus for the TATA-box binding protein, the DNA bining subunit of TFIID and a component of SLI and TFIIIB, strongly suggests that it is single copy in the human genome. *Genomics* 22, 94–100 (1994).
21. Trachtulec, Z. et al. Linkage of TATA-binding protein and proteasome subunit C5 genes in mice and humans reveals synteny conserved between mammals and invertebrates. *Genomics* 44: 1–7 (1997).
22. Owens, G. P., Hahan, W. E., & Cohen, J. J. Identification of mRNAs associated with programmed cell death in immature thymocytes. *Mol. Cell. Biol.* 11, 4177–4188 (1991).
23. Chalut, C., Gallois, Y., Poterszman, A., Moncollin, V. & Egly, J. -M. Genomic structure of the human TATA-box-binding protein (TBP). *Gene* 161, 277–282 (1995).
24. Schmidt, E. E. & Schibler, U. High accumulation of components of the RNA polymerase II transcription machinery in rodent spermatids. *Development* 121, 2373–2383 (1995).
25. Biamonti, G., Ruggiu, M., Saccone, S., Della Valle, G. & Riva, S. Two homologous genes, originated by duplication, encode the human hnRNP proteins A2 and A1. *Nucleic Acids Res.* 22, 1996–2002(1994).
26. Kozu, T., Henrich, B. & Schafer, K. P. Structure and expression of the gene (HNRPA2B1) encoding the human hnRNP protein A2/B1. *Genomics* 25, 365–371 (1995).
27. Ye, Q. & Worman, H. J. Interaction between an integral protein of the nuclear envelope inner membrane and human chromodomain proteins homologous to Drosophila HP1. *J. Biol. Chem.* 271, 14653–14656 (1996).
28. James, T. C. & Elgin, S. C. R. Identification of a nonhistone chromosomal protein associated with heterochromatin in *Drosophila melanogaster* and its gene. *Mol. Cell. Biol.* 6, 3861–3872 (1986).
29. Singh, P. B., et al. A sequence motif found in a drosophila heterochromatin protein is conserved in animals and plants. *Nucleic Acids Res.* 19, 789–794 (1991).
30. Gilliand, G., Perrin,m S., Blanchard, K. & Bunn, H. F. Analysis of cytokine Mrna and DNA: detection and quantitation by competitive polymerase chain reaction. *Proc. Natl. Acad. Sci. USA* 87, 2725–2729 (1990).
31. Furth, P. A. Hennighausen, L., Baker, C., Beatty, B. & Woychick, R. The viarability in activity of the universally expressed human cytomegalovirus immediate early gene I promoter/enhancer in transgenic mice. *Nucleic Acids Res.* 19 6205–6208 (1991).
32. Ray, P. et al. Ectopic expression of a c-kit $^{W42}$ minigene in transgenic mice: recapitulation of W phenotypes and evidence for c-kit function in melanoblast progenitors. *Genes Dev.* 5, 2265–2273 (1991).
33. Yamashita, T. et al. High level expression of human a-fetoprotein in transgenic mice. *Biochem, Biophys. Res. Comm.* 191, 715–720 (1993).
34. Milot, E. et al. Heterochromatin effects on the frequency and duration of LCR-mediated gene transcription. *Cell* 87, 104–114 (1996).
35. Festenstein, R. et al. Locus control region function and heterochromatin-induced position effect variegation. *Science* 271, 1123–1125 (1996).
36. Sabbattini, P., Georgiou, A., Sinclaire, C. & Dillon, N. Analysis of mice with single and multiple copies of transgenes reveals a novel arrangement for the λ5–V-preBI locus control region. *Mol. Cell. Biol.* 19, 671–679 (1999).
37. Ng, S. Y. et al. Evolution of the functional human β-actin gene and its multi-pseudogene family: conservation of noncoding regions and chromosomal dispersion of pseudogenes. *Mol. Cell. Biol.* 5, 2720–2732 (1985).
38. Pravtcheva, D. D., Wise, T. L., Ensor, N. J. & Ruddle, F. H. Mosaic expression of an HPRT transgene integrated in a region of Y heterochromatin. *J. Exp. Zool.* 268, 452–468 (1994).
39. Bell, A. C. & Felsenfield, G. Stopped at the border: boundaries and insulators. *Curr. Opin. Genet. Dev.* 9, 191–198 (1999).
40. Winston, J. H., Hong, L., Datta, S. K. & Kellems, R. E. An intron 1 regulatory region from the murine adenosine deaminase gene can activate heterologous promoters for ubiquitous expression in transgenic mice. *Somat. Cell Mol. Genet.* 22, 261–278 (1996).
41. Hart, C. M. & Laemmli, U. K. Facilitation of chromatin dynamics by SARs. *Curr. Opin. Genet. Develop.* 8,519–525 (1998).
42. Klehr, D., Maass, K. & Bode, J. Scaffold-attached regions from the human interferon β domain can be used to enhance the stable expression of genes under the control of various promoters. *Biochemistry* 30, 1264–1270 (1991).
43. McKnight, R. A., Shamay, L., Sankaran, L., Wall, R. J. & Henninghausen, L. Matrix-attachment regions can impart position-independent regulation of a tissue-specific gene in transgenic mice. *Proc. Natl. Acad. Sci. USA* 89, 6943–6947 (1992).
44. Van Drunen, C. M., et al. A bipartite sequence element associated with matrix/scaffold attachment regions. *Nucleic Acids Res.* 27, 2924–2930 (1999).
45. Verma, I. M. & Somia, N. Gene Therapy—promises, problems and prospects. *Nature* 389: 239–242 (1997).
46. Brown, S. A. & Kingston, R. E. Disruption of downstream chromatin directed by a transcriptional activator. *Genes Dev.* 11.3 116–3121 (1997).
47. Orphanides, G., LeRoy, G., Chang, C. H., Luse, D. S. & Reinberg, D. FACT, a factor that facilitates transcript elongation through nucleosomes. *Cell* 92, 105–116 (1998).
48. Schnitzler, G., Sif, S. & Kingston, R. E. Human SWI/SNF interconverts a nucleosome between its base state and a stable remodelled state. *Cell* 94, 17–27 (1998).
49. Travers, A. Chromatin modification by DNA tracking. *Proc. Natl. Acad. Sci. USA* 96, 13634–13637 (1999).

50. Ashe, H. L., Monks, J., Wijgerde, M., Fraser, P. & Proudfoot, N. J. Intergenic transcription and transinduction of the human β-globin locus. *Genes Dev* 11, 2494–2509 (1997).
51. Rogan, D. F., Cousins, D. J. & Staynov, D. Z. Intergenic transcription occurs throughout the human IL-4/IL-13 gene cluster. *Biochem. Biophys. Res. Commun.* 255, 556–561 (1999).
52. Gribnau, J., Diderich, K., Pruzina, S., Calzorlari, R. & Fraser P. Intergenic transcription and developmental remodeling of chromatin subdomains in the human β-globin locus. *Mol. Cell* 5, 377–386 (2000).
53. Vyas, P. et al. Cis-acting sequences regulating expression of the human α-globin cluster lie within constitutively open chromatin. *Cell* 69, 781–793 (1992).
54. Ioannou, P. A. et al. A new bacteriophage P1–derrived vector for the propagation of large human DNA fragments. *Nature Gene.* 6, 84–89 (1994).
55. Raguz, S. et al. Muscle-specific locus control region activity associated with the human desmin gene. *Dev. Biol.* 201, 26–42 (1998).
56. Dillon, N. & Grosveld, F. Transcriptional analysis using transgenic animals, in Gene Transcription: A practical approach (eds. Hames, B. D. & Higgins, S. J.) pp. 153–188 (IRL Press, Oxford, 1993).
57. Morgenstern, J. P. & Land, H. Advanced mammalian gene transfer: high titre retroviral vectors with multiple drug selection markers and a complementary helper-free packaging cell line. *Nucleic Acids Res* 18, 3587–3595 (1990).
58. Horz, W. & Altenburger, W. Nucleotide sequence of mouse satellite DNA. *Nucleic Acids Res.* 9, 683–696 (1981).
59. Monfouilloux, S. et al. Recent human-specific spreading of a subtelomeric domain. *Genomics* 51, 165–176 (1998).

What is claimed is:

1. A polynucleotide comprising a ubiquitous chromatin opening element (UCOE) comprising an extended methylation free CpG-island, which opens chromatin or maintains chromatin in an open state and facilitates reproducible expression of an operably-linked gene in cells of at least two different tissue types, wherein the nucleotide sequence of the UCOE does not occur in nature.

2. The polynucleotide of claim 1, which facilitates reproducible expression of an operably-linked gene non-tissue specifically.

3. The polynucleotide of claim 1, which facilitates reproducible expression of an operably-linked gene in all tissue types where active gene expression occurs.

4. The polynucleotide of claim 1, which facilitates expression of an operably-linked gene at a physiological level.

5. The polynucleotide of claim 1, wherein the UCOE comprises an extended methylation-free, CpG-island.

6. The polynucleotide of claim 1, wherein the UCOE comprises at least one naturally-occurring sequence associated with the control of gene expression.

7. The polynucleotide of claim 1, wherein the UCOE comprises at least one naturally-occurring promoter.

8. The polynucleotide of claim 1, wherein the UCOE comprises dual or bi-directional promoters that transcribe divergently.

9. The polynucleotide of claim 1, wherein the UCOE comprises the human β-actin CpG island/promoter region or a fragment thereof.

10. The polynucleotide of claim 9, wherein the UCOE comprises a DNA fragment within the range of 100 bp to 3.0 kb spanning the human β-actin CpG island/promoter region or a fragment thereof.

11. The polynucleotide of claim 1, wherein the UCOE comprises the human PCDC2 CpG island/promoter region or a fragment thereof.

12. The polynucleotide of claim 11, wherein the UCOE comprises a DNA fragment within the range of 100 bp to 3.0 kb spanning the human PCDC2 CpG island/promoter region or a fragment thereof.

13. The polynucleotide of claim 1, wherein the UCOE comprises a DNA fragment within the range of 100 bp to 3.0 kb spanning the human β-actin CpG island/promoter region and a DNA fragment within the range of 100 bp to 3.0 kb spanning the human PDCD2 CpG island/promoter region.

14. The polynucleotide of claim 1, wherein the UCOE comprises a 2.0 kb DNA fragment spanning the human β-actin CpG island/promoter region and a 1.8 kb DNA fragment spanning the human PDCD2 CpG island/promoter region.

15. The polynucleotide of claim 13 or claim 14 wherein the promoters are orientated divergently.

16. The polynucleotide of claim 1, wherein the UCOE comprises SEQ ID NO:1 or a fragment thereof in either orientation.

17. The polynucleotide of claim 1, wherein the UCOE comprises the human RNP CpG island/promoter region or a fragment thereof.

18. The polynucleotide of claim 17, wherein the UCOE comprises a 4 kb DNA fragment spanning the human RNP CpG island/promoter region.

19. The polynucleotide of claim 1, comprising an extended methylation-free CpG island containing bidivergent promoters adjacent to at least one further sequence comprising a methylation-free CpG island.

20. The polynucleotide of claim 1, wherein the UCOE comprises the human RNP CpG island/promoter region and a DNA fragment in the range 100 bp to 3.0 kb spanning the human β-actin CpG island/promoter region.

21. The polynucleotide of claim 20, wherein the UCOE comprises SEQ ID NO:2 or fragment thereof in either orientation.

22. The polynucleotide of claim 1, further comprising a promoter.

23. The polynucleotide of claim 1, wherein the UCOE comprises at least one promoter sequence mutated to be incapable of initiating transcription.

24. The polynucleotide of claim 22 or claim 23 wherein the promoter is the CMV promoter.

25. The polynucleotide of claim 24 wherein the promoter is the mouse CMV promoter.

26. The polynucleotide of claim 1, wherein the UCOE comprises at least one sequence which is artificially synthesized.

27. A vector comprising the polynucleotide of claim 1.

28. The vector of claim 27, further comprising an expressible gene operably-linked to a promoter and the polynucleotide.

29. The vector of claim 27 or claim 28 wherein the vector is an episomal or integrating vector.

30. The vector according to claim 27, wherein the vector is a plasmid.

31. The vector according to claim 27, wherein the vector is a virus.

32. The vector according to claim 28, wherein the operably-linked gene is a therapeutic nucleic acid sequence.

33. The vector of claim 27, wherein the UCOE is effective in both orientations, said vector further comprising
 a) a first and a second promoter, said arranged to transcribe divergently; and
 b) a first and a second site for insertion of open reading frames to be expressed, wherein each of said first and second promoters is operably-linked to the UCOE,
 wherein the first site for insertion is under the control of the first promoter, and the second site for insertion is under the control of the second promoter, and further wherein the UCOE is situated between the first and second promoter.

34. The vector of claim 33, further comprising a nucleic acid encoding an immunoglobulin heavy chain inserted into the first site for insertion, and a nucleic acid encoding an immunoglobulin light chain inserted into the second site for insertion.

35. The vector of claim 27, comprising SEQ ID NO:1, the CMV promoter, a multiple cloning site, a polyadenylation sequence and genes encoding selectable markers under suitable control elements.

36. The vector of claim 27, comprising SEQ ID NO:2, the CMV promoter, a multiple cloning site, a polyadenylation sequence and genes encoding selectable markers under suitable control elements.

37. The vector of claim 35 or claim 36, wherein the orientation of the UCOE is reversed.

38. The vector CET 500.

39. The vector CET 501.

40. The vector CET 600.

41. The vector CET 601.

42. A host cell transfected with the vector of any one of claims 27 or 38–41.

43. A composition comprising the polynucleotide of claim 1.

44. A composition comprising the host cell of claim 42, in combination with a pharmaceutically acceptable excipient.

45. A method of obtaining a desired gene product comprising using the polynucleotide of claim 1.

46. A method of obtaining a desired gene product comprising using the host cell of claim 42 in a cell culture system in order to obtain a desired gene product.

47. A nucleic acid molecule comprising a DNA sequence selected from the group consisting of SEQ ID NO:1 and SEQ ID NO:2.

48. A method for preparing a polypeptide comprising:
providing a cell transformed/transfected with the nucleic acid molecule according to claim 47;
growing said cell in conditions conducive to the production of said polypeptide; and
purifying said polypeptide from said cell, or its growth environment.

49. A composition comprising the vector of any one of claims 27 or 38–41, in combination with a pharmaceutically acceptable excipient.

50. A method of obtaining a desired gene product comprising using the vector of any one of claims 27 or 38–41 in a cell culture system in order to obtain a desired gene product.

* * * * *